US008343038B2

(12) United States Patent
Segawa

(10) Patent No.: US 8,343,038 B2
(45) Date of Patent: Jan. 1, 2013

(54) POWER SUPPLY STARTER FOR CAPSULE ENDOSCOPE

(75) Inventor: Hidetake Segawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 1476 days.

(21) Appl. No.: 11/631,059

(22) PCT Filed: Jan. 19, 2006

(86) PCT No.: PCT/JP2006/300769
§ 371 (c)(1),
(2), (4) Date: Feb. 12, 2007

(87) PCT Pub. No.: WO2006/087884
PCT Pub. Date: Aug. 24, 2006

(65) Prior Publication Data
US 2009/0192353 A1 Jul. 30, 2009

(30) Foreign Application Priority Data

Feb. 16, 2005 (JP) ................................. 2005-039508

(51) Int. Cl.
*A61B 1/00* (2006.01)
*A61B 1/04* (2006.01)
(52) U.S. Cl. ........................ 600/118; 600/121; 600/109
(58) Field of Classification Search ............ 600/118, 600/109, 102, 103; 348/74, 76
See application file for complete search history.

(56) References Cited

U.S. PATENT DOCUMENTS

| 4,697,703 A * | 10/1987 | Will ............................. 206/438 |
| 5,082,112 A * | 1/1992 | Dunklee ....................... 206/363 |
| 5,221,007 A * | 6/1993 | Foos ............................ 206/363 |
| 6,918,872 B2 * | 7/2005 | Yokoi et al. .................. 600/129 |
| 7,009,634 B2 * | 3/2006 | Iddan et al. .................. 348/76 |
| 7,295,226 B1 * | 11/2007 | Meron et al. .................. 348/77 |
| 7,354,398 B2 * | 4/2008 | Kanazawa ..................... 600/109 |
| 7,766,167 B2 * | 8/2010 | Segawa ......................... 206/439 |
| 7,770,725 B2 * | 8/2010 | Segawa ......................... 206/363 |
| 2001/0035902 A1 | 11/2001 | Iddan et al. |
| 2004/0087832 A1 | 5/2004 | Glukhovsky et al. |

(Continued)

FOREIGN PATENT DOCUMENTS

EP 1 834 568 A1 9/2007

(Continued)

OTHER PUBLICATIONS

Extended Supplementary European Search Report dated Sep. 29, 2009.

(Continued)

*Primary Examiner* — Philip R Smith
*Assistant Examiner* — William Chou
(74) *Attorney, Agent, or Firm* — Scully Scott Murphy & Presser, PC

(57) ABSTRACT

A power supply starter (51) provided with a magnetic body (51e) is mounted on an inner lid portion (42) while a sterilizing sheet (43) is opened for enabling application of a magnetic field from outside of the inner lid portion (42) (inside of the inner lid portion (42)) by the magnetic body (51e), and therefore, the start to drive respective functions of the capsule endoscope (2) is prevented until the magnetic field is applied from outside, and thereby, the start to drive the respective functions of the capsule endoscope can be performed with arbitrary timing and the consumption of power accumulated within the capsule endoscope can be suppressed.

16 Claims, 18 Drawing Sheets

U.S. PATENT DOCUMENTS

| | | | |
|---|---|---|---|
| 2004/0138558 A1* | 7/2004 | Dunki-Jacobs et al. | 600/431 |
| 2004/0158138 A1* | 8/2004 | Kilcoyne et al. | 600/350 |
| 2004/0254455 A1* | 12/2004 | Iddan | 600/424 |
| 2005/0272973 A1 | 12/2005 | Kawano et al. | |
| 2006/0258901 A1* | 11/2006 | Fujimori et al. | 600/101 |
| 2007/0225552 A1* | 9/2007 | Segawa et al. | 600/102 |
| 2007/0270641 A1* | 11/2007 | Kimoto et al. | 600/109 |
| 2008/0033243 A1* | 2/2008 | Meron et al. | 600/109 |
| 2009/0118581 A1* | 5/2009 | Meron et al. | 600/109 |

FOREIGN PATENT DOCUMENTS

| | | |
|---|---|---|
| EP | 1 834 569 A1 | 9/2007 |
| JP | 2003-210395 A1 | 7/2003 |
| JP | 2003-523795 A | 8/2003 |
| JP | 2004-148124 | 5/2004 |
| JP | 2004-261240 A | 9/2004 |
| JP | 200694933 A * | 4/2006 |
| WO | WO 01/35813 A1 | 5/2001 |
| WO | WO 2004/075739 A1 | 9/2004 |
| WO | WO 2004/086434 A2 | 10/2004 |

OTHER PUBLICATIONS

Decision on Patent Grant dated Jun. 22, 2010 together with an English language translation.

Japanese Office Action dated Oct. 23, 2009 together with English translation.

Extended European Search Report dated Jun. 29, 2011 for European Application No. EP 11 00 3496.4.

* cited by examiner

POWER SUPPLY STARTER FOR CAPSULE ENDOSCOPE

TECHNICAL FIELD

The present invention relates to a power supply starter for capsule endoscope for starting power supply to respective function executing units of a capsule endoscope, for example, of type to be swallowed that is introduced into a subject and acquires image information within the subject.

BACKGROUND ART

Recently, in the field of endoscope, a capsule endoscope having an imaging function and a wireless transmission function has appeared. The capsule endoscope is configured to be swallowed by an examinee as a subject for observation (examination), then, move inside organs (within body cavity) such as stomach and small bowel with the peristaltic motion thereof in an observation period until the endoscope is naturally discharged from the living body of the examinee, and sequentially image using the imaging function.

Further, in the observation period by the movement within these organs, image data imaged within the body cavity by the capsule endoscope is sequentially transmitted to an external device provided outside of the subject by the wireless transmission function such as wireless communication, and accumulated in a memory provided within the external device. The examinee carries the external device having the wireless transmission function and the memory function, and therefore, the examinee is able to act without inconvenience in the observation period after the examinee swallows the capsule endoscope and before discharges it. After observation, a doctor or nurse is able to display images within the body cavity based on the image data accumulated in the memory of the external device on display means such as a display and make diagnoses.

In this type of capsule endoscope, for example, there is one to be swallowed as shown in Patent Document 1. In order to control the driving of the capsule endoscope, a configuration having a reed switch turned on and off by an external magnetic field therein and accommodated in a package including a permanent magnet for supplying the external magnetic field has been proposed. That is, the reed switch within the capsule endoscope has a structure that maintains the off-state under the environment in which a magnetic field having predetermined intensity or more is provided and turns on due to reduction in the intensity of the external magnetic field. Accordingly, in the condition in which the capsule endoscope is accommodated in the package, the capsule endoscope is not driven. When the capsule endoscope is taken out from the package at the time of being swallowed, the capsule endoscope is spaced from the permanent magnet, no longer affected by the magnetic force, and started to be driven. The capsule endoscope has such a configuration, and therefore, the capsule endoscope can be prevented from being driven when it is accommodated within the package, and imaging of images by the imaging function of the capsule endoscope and transmission of image signals by the wireless transmission function are performed after it is taken out from the package.

Patent Document 1: International Publication No. 01/35813 Pamphlet

DISCLOSURE OF INVENTION

Problem to be Solved by the Invention

However, in the above described device, there has been a problem that power accumulated within the capsule endoscope is wasted because certain time is needed after the capsule endoscope is taken out from the package and before it is introduced into the subject, and the respective functions of the capsule endoscope such as the imaging function and the wireless transmission function are started to be driven during the time and imaging operation of images is carried out by the imaging function and wireless transmission operation of image signals obtained by the wireless transmission function is further carried out.

The invention has been achieved in view of the above described problem, and it is an object to provide a power supply starter for capsule endoscope capable of suppressing consumption of power accumulated within a capsule endoscope by enabling the start to drive the respective functions of the capsule endoscope with arbitrary timing by applying a magnetic field to the capsule endoscope to supply power to an executing unit of the respective functions.

Means for Solving Problem

A power supply starter for capsule endoscope according to the present invention includes a magnetic body in a capsule endoscope, the magnetic body being capable of applying a magnetic field from outside of a holder, the capsule endoscope being held by the holder within a container case and including a switch for power supply, the switch switching power supply state when applied with the magnetic field.

Further, in the power supply starter for capsule endoscope according to the invention, the holder may have a first holder and a second holder which form a holding space region in between for accommodating and holding the capsule endoscope within the holding space region. The power supply starter for capsule endoscope may detachably engage with one of the first and second holders.

Further, the power supply starter for capsule endoscope according to the invention may further include a movement portion allowing the magnetic body to move; and an inhibiting portion for inhibiting a movement of the magnetic body. When the power supply starter contacts the container case, inhabitation by the inhibiting portion may be released and the magnetic body moves by the movement portion so as to switch the switch for power supply to a power supply state.

Further, in the power supply starter for capsule endoscope the magnetic body may include at least two magnetic bodies opposed to each other with the capsule endoscope being in between.

Further, the power supply starter for capsule endoscope according to the invention may include a confirming unit capable of confirming the power supply state of the capsule endoscope.

Effect of the Invention

The power supply starter for capsule endoscope according to the present invention enables the approached magnetic body of the power supply starter to apply a magnetic field from outside of the holder to the switch for power supply of the capsule endoscope held by the holder within the container case, and thereby, the start to drive respective functions of the capsule endoscope is prevented until the magnetic field is applied from outside and an effect that the consumption of power accumulated within the capsule endoscope can be suppressed is exerted.

EXPLANATIONS OF LETTERS OR NUMERALS

Figure 1:
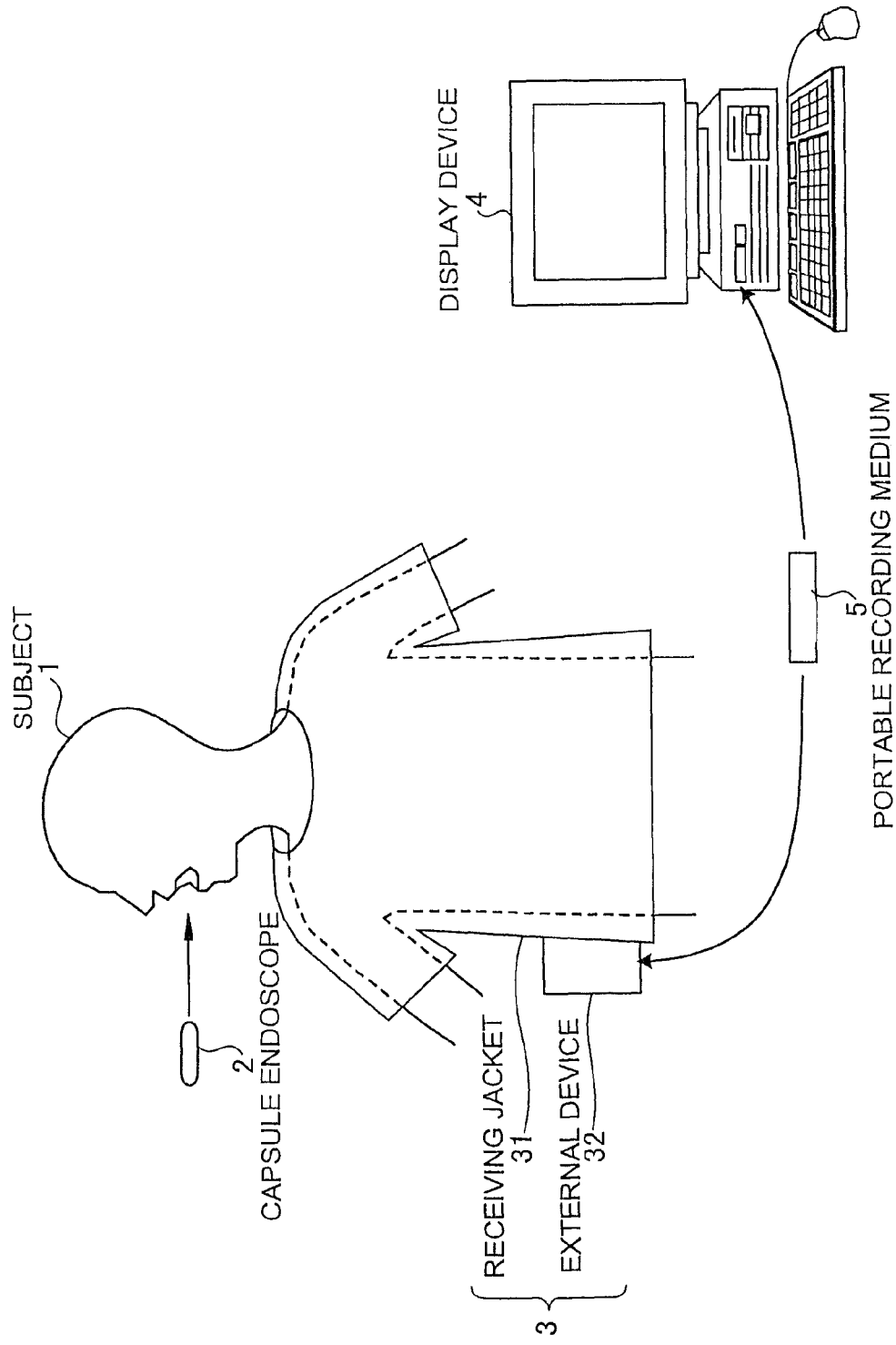
FIG. 1 is a system conceptual diagram showing a concept of a wireless in-vivo information acquiring system according to the present invention.

1 Subject
2 Capsule endoscope
2a Reed switch
2b Power supply operable range
3 Receiving device
4 Display device
5 Portable recording medium
11 Sealed container
11a Front cover
11a1 Mirror finish portion
11b Barrel portion cover
20 Light emitting element (LED)
21 LED driving circuit
22 Solid state image sensor
23 CCD driving circuit
24 RF transmission unit
25 Transmission antenna
26 System control circuit
26b, 26c Flip-flop
27 Imaging lens
29 Battery
31 Receiving jacket
32 External device
40 Container case
40a Holding space region
40b Path
41 Blister pack
41a, 42a, 51b Cylindrical portion
41b, 42b, 51a Tab portion
41c, 42c Rim portion
41d, 42d, 41e4 Projection portion
41e, 42e Bottom surface
41e1 Outer bottom surface
41e2 Inner bottom surface
41e3 Holding portion
41e5, 42e2, 42g, 51f, 51i Projection
42 Inner lid portion
42e1 Projecting portion
42e3 Step portion
42f, 51g, 51h1 Groove
42h Step portion
43 Sterilizing sheet
51 Power supply starter
51c Hole portion
51d Bottom surface
51e, 51h2, 52a, 52b Magnetic body
51j Reflection mirror
51h3 Claw portion

BEST MODE(S) FOR CARRYING OUT THE INVENTION

As below, embodiments of a power supply starter for capsule endoscope and a container case according to the present invention will be described in detail based on the drawings of FIGS. 1 to 27. Note that the invention is not limited to these embodiments and various changes may be made to embodiments without departing from the scope of the invention.

First Embodiment

FIG. 1 is a system conceptual diagram showing a concept of a wireless in-vivo information acquiring system according to the invention. In FIG. 1, the capsule endoscope system includes a swallowable capsule endoscope 2 as a wireless in-vivo information acquiring device to be introduced into a body cavity of a subject 1, and a receiving device 3 as an external device located outside of the subject 1 and wirelessly communicating various kinds of information with the capsule endoscope 2. Further, the wireless in-vivo information acquiring system includes a display device 4 for image display based on data received by the receiving device 3 and a portable recording medium 5 for inputting and outputting data between the receiving device 3 and the display device 4.

As shown in the side sectional view of FIG. 2, the capsule endoscope 2 includes a sealed container 11 as an outer case, and component elements such as plural light emitting elements 20 such as LEDs that output illumination light for illuminating a part to be examined within a body cavity, a solid state image sensor 22 such as a CCD or CMOS for receiving the reflection light of the illumination light and imaging the part to be examined (hereinafter, representatively referred to as "CCD 22"), an imaging lens 27 for forming images of the subject onto the CCD 22, an RF transmission unit 24 for modulating image information acquired by the CCD 22 into RF signals and transmitting the information, a transmission antenna 25 for emitting electric wave of the RF signals, and a battery 29, for example, located within the sealed container 11.

The sealed container 11 has a size that can be swallowed by humans, and forms an outer case for liquid-tight sealing the interior by elastically fitting a front cover 11a having a nearly semispherical shape and a tubular barrel portion cover 11b. The front cover 11a has a nearly semispherical dome shape, and the rear side of the dome circularly opens. The front cover 11a has a mirror finish portion 11a1 shaped by a transparent member having transparency or translucency, for example, cycloolefin polymer or polycarbonate that is preferable for securing optical performance and strength, and having a mirror finished surface, which will be described later. Thereby, the illumination light from the light emitting elements 20 can be transmitted to the outside of the sealed container 11 and the reflection light of the illumination light from the subject can be transmitted to the inside thereof. The mirror finish portion 11a1 is formed in a predetermined mirror finish range (the range shown by dashed lines a, a in FIG. 2) that is determined depending on the imaging range of the solid state image sensor 22 or the like.

Further, the barrel portion cover 11b is a member located at the rear end of the front cover 11a for covering the component elements. The barrel portion cover 11b integrally forms a barrel part having a cylindrical shape and a rear end portion having a nearly semispherical dome shape, and the front side of the barrel part circularly opens. The barrel portion cover 11b is formed by polysulfone that is preferable for securing strength, and accommodates an illuminating unit, imaging unit, and the battery 29 in the barrel part and accommodates a wireless transmitting unit in the rear end portion, which will be described later.

Figure 3:
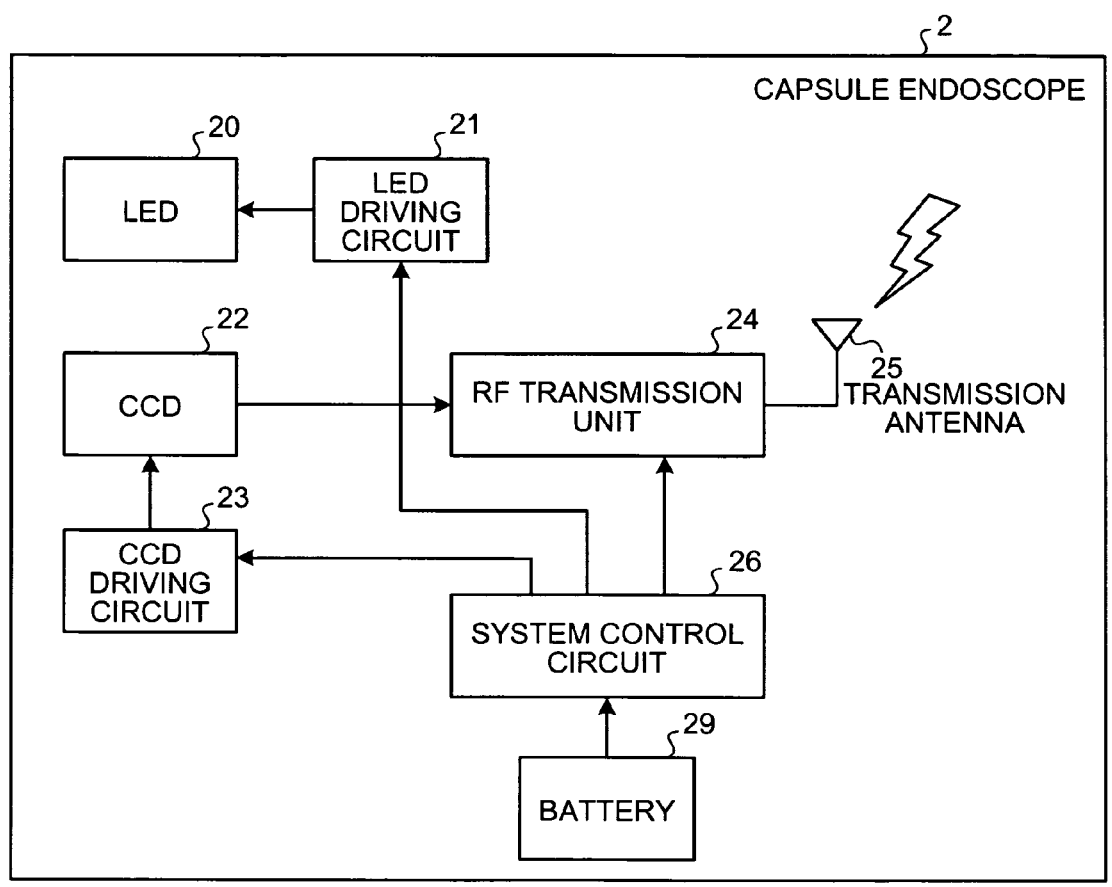
FIG. 3 is a block diagram showing an interior configuration of the capsule endoscope shown in FIG. 2.

As shown in a block diagram of FIG. 3, the capsule endoscope 2 includes the LEDs 20 as the illuminating unit and an LED driving circuit 21 for controlling the drive state of the LEDs 20, the CCD 22 as the imaging unit for imaging images within a body cavity (information within a subject) as reflection light from regions illuminated by the LEDs 20 via an imaging lens 27 and a CCD driving circuit 23 for controlling the drive state of the CCD 22, the RF transmission unit 24 as the wireless transmission unit, and the transmission antenna 25 within the sealed container 11.

Further, the capsule endoscope 2 includes a system control circuit 26 for controlling the operation of these LED driving circuit 21, CCD driving circuit 23, and RF transmission unit 24, and thereby, operates to acquire image data of a part to be examined illuminated by the LEDs 20 by the CCD 22 while the capsule endoscope 2 is being introduced into the subject 1. The acquired image data is further converted into RF signals by the RF transmission unit 24 and transmitted to the outside of the subject 1 via the transmission antenna 25. Furthermore, the capsule endoscope 2 includes the battery 29 for supplying power to the system control circuit 26, and the system control circuit 26 has a function of distributing the drive power supplied from the battery 29 to the other component elements (function executing unit).

The system control circuit 26 includes a switch element and a latch circuit having a switching function connected between the respective component elements and the battery 29, for example. The latch circuit turns the switch element on when an external magnetic field is applied thereto, and subsequently maintains the on-state for supplying the drive power from the battery 29 to the respective component elements within the capsule endoscope 2. In this embodiment, the imaging unit having the imaging function, the illuminating unit having the illuminating function, the wireless transmitting unit having the wireless transmission function provided within the capsule endoscope 2 are collectively referred to as a function executing unit for executing predetermined functions. Specifically, except the system control circuit 26, they are the function executing units for executing preset predetermined functions.

As shown in FIG. 1, the receiving device 3 has a function as a wireless receiving unit for receiving image data within the body cavity wirelessly transmitted from the capsule endoscope 2. The receiving device 3 is worn by the subject 1, and includes a receiving jacket 31 having plural receiving antennas (not shown) and an external device 32 for performing signal processing of the received radio signals or the like.

The display device 4 is for displaying images within body cavity imaged by the capsule endoscope 2, and has a configuration such as a workstation for performing image display based on data obtained by the portable recording medium 5. Specifically, the display device 4 may have a configuration for directly displaying images by a CRT display, liquid crystal display, or the like, or may have a configuration for outputting images to other media such as a printer.

The portable recording medium 5 is connectable to the external device 32 and the display device 4, and has a structure capable of outputting or recording information when mounted on and connected to both of them. In this embodiment, the portable recording medium 5 is inserted into the external device 32 for recording the data transmitted from the capsule endoscope 2 while the capsule endoscope 2 moves within the body cavity of the subject 1. After the capsule endoscope 2 is discharged from the subject 1, that is, after imaging within the subject 1 is finished, the portable recording medium 5 is discharged from the external device 32 and inserted into the display device 4, and the data recorded in the portable recording medium 5 by the display device 4. For example, the portable recording medium 5 includes a CompactFlash® memory, and is able to indirectly input data to and output data from the external device 32 and the display device 4 via the portable recording medium 5. Unlike the case where the external device 32 and the display device 4 are directly wired, the subject 1 is able to freely act during imaging within the body cavity.

Figure 8:
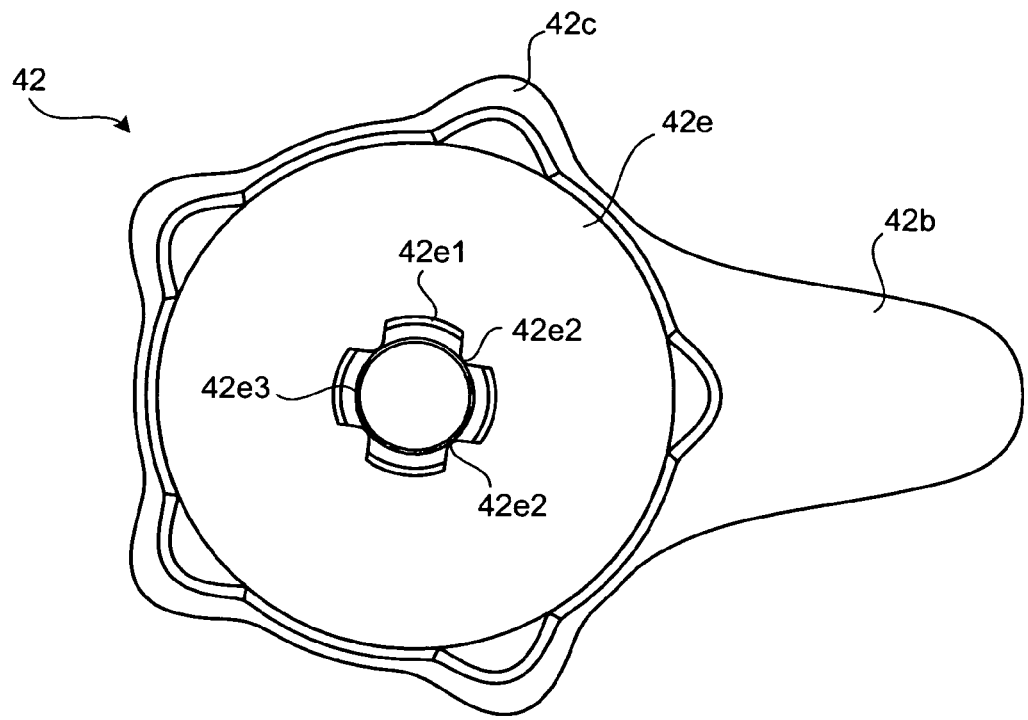
FIG. 8 is a top view showing the top of an inner lid portion shown in FIG. 5 according to a first embodiment.
Figure 9:
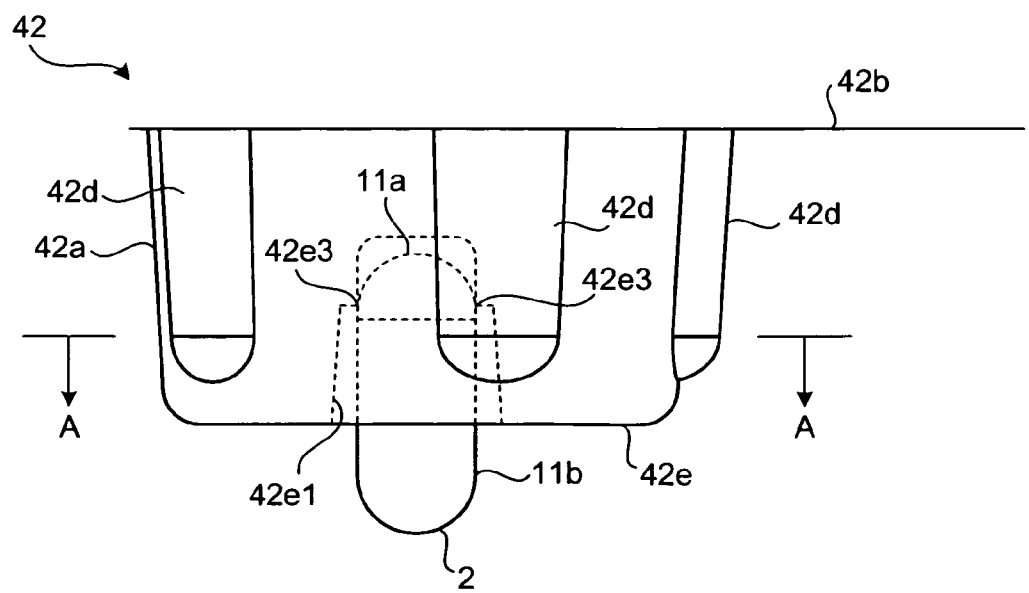
FIG. 9 is similarly a side view showing the side of the inner lid portion according to the first embodiment.
Figure 10:
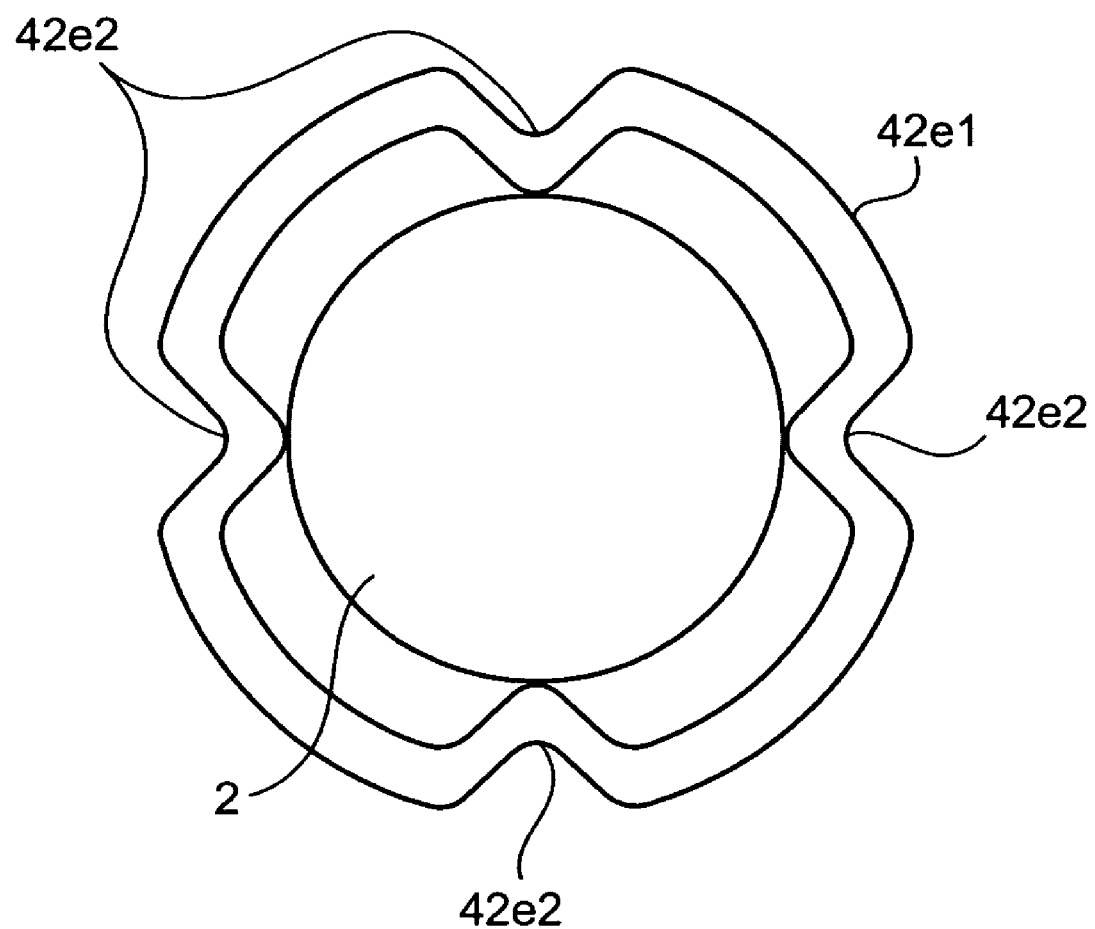
FIG. 10 is a sectional view showing enlarged A-A section of a hole portion shown in FIG. 9.
Figure 11:
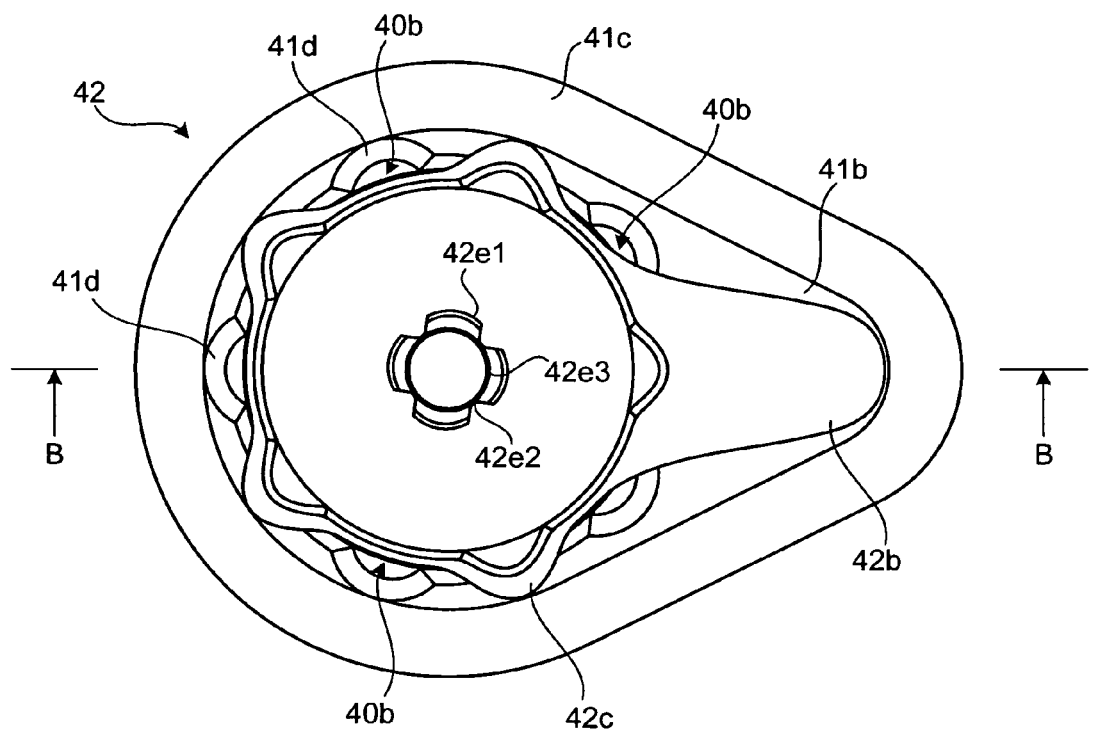
FIG. 11 is a top view showing the top of the container case shown in FIG. 5.
Figure 12:
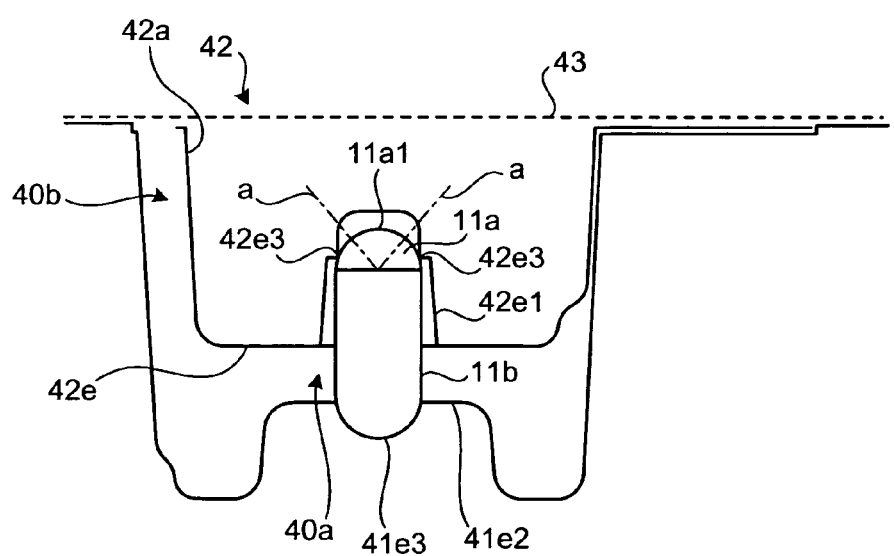
FIG. 12 is a sectional view showing enlarged B-B section in FIG. 11.

By the way, it is necessary to sterilize a capsule endoscope including the function executing unit and keep the sterilized condition before use for a subject. Accordingly, in the embodiment, the above described capsule endoscope 2 is accommodated in a container case that can be sterilized. As below, the container case according to First embodiment will be described using FIGS. 4 to 12. Here, FIG. 4 is a perspective view showing a configuration of a container case for accommodating the capsule endoscope, FIG. 5 is a perspective view showing an example of the case where a sterilizing sheet is removed from the container case shown in FIG. 4, FIG. 6 is a top view showing the top of the container case shown in FIG. 5, FIG. 7 is similarly a side view showing the side of the container case, FIG. 8 is a top view showing the top of an inner lid portion shown in FIG. 5 according to the first embodiment, FIG. 9 is similarly a side view showing the side of the inner lid portion according to the first embodiment, FIG. 10 is a sectional view showing enlarged A-A section of a hole portion shown in FIG. 9, FIG. 11 is a top view showing the upper surface of the container case shown in FIG. 5, and FIG. 12 is a sectional view showing B-B section in FIG. 11.

Figure 4:
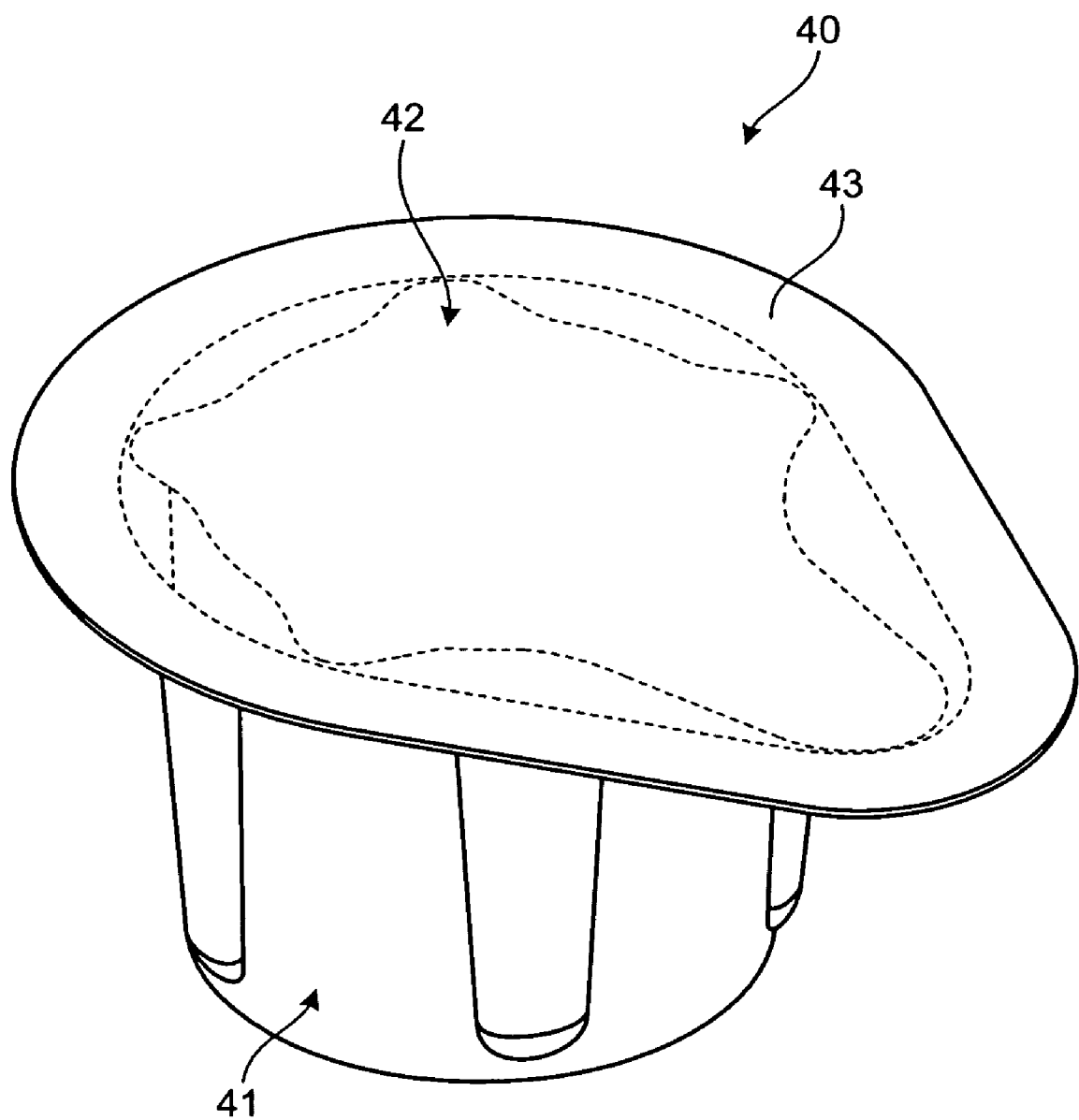
FIG. 4 is a perspective view showing a configuration of a container case for accommodating the capsule endoscope.
Figure 5:
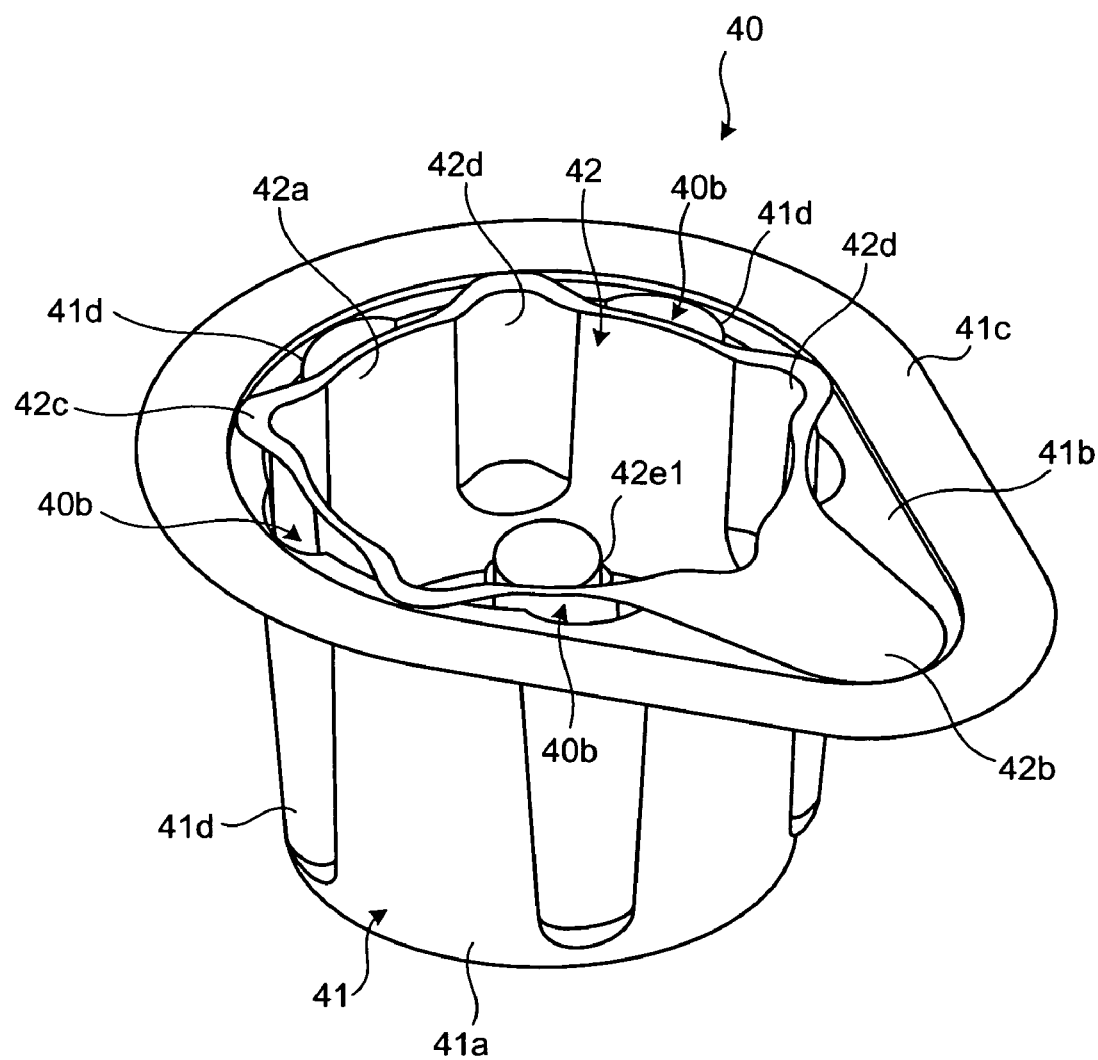
FIG. 5 is a perspective view showing an example when a sterilizing sheet is removed from the container case shown in FIG. 4.

First, in FIGS. 4 and 5, a container case 40 includes a blister pack 41 having an external container that can accommodate the capsule endoscope 2 within, an inner lid portion 42 provided within the blister pack 41 and including an inner container for holding the capsule endoscope 2 between the blister pack 41 and itself, and a sterilizing sheet 43 provided on the upper surface of the blister pack 41 for closing the opening of the blister pack 41. The blister pack 41 and the inner lid portion 42 are first and second holders according to the invention, and formed by a material of polypropylene by molding processing such as vacuum molding, for example.

Figure 6:
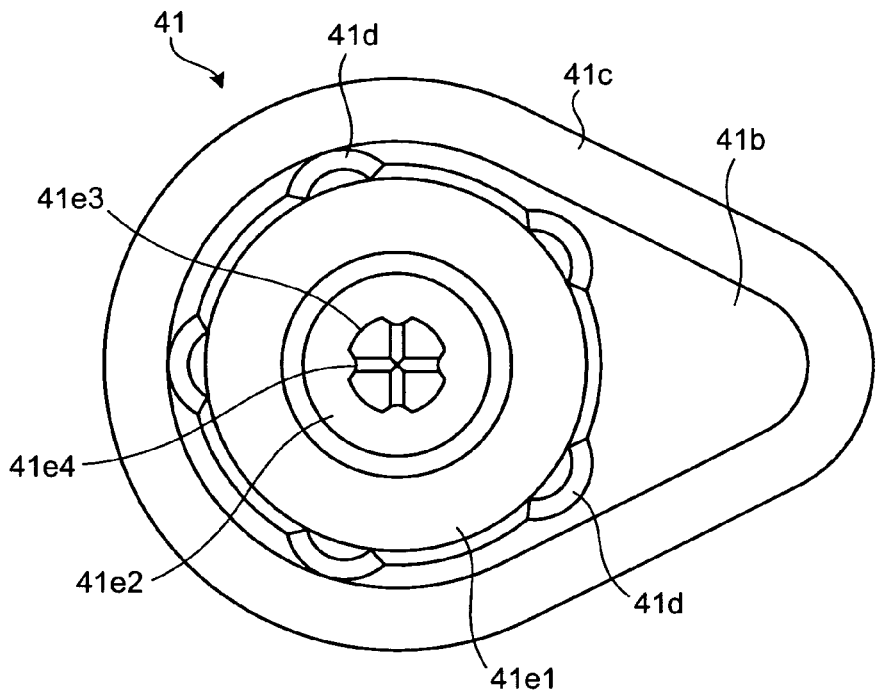
FIG. 6 is a top view showing the top of the container case shown in FIG. 5.
Figure 7:
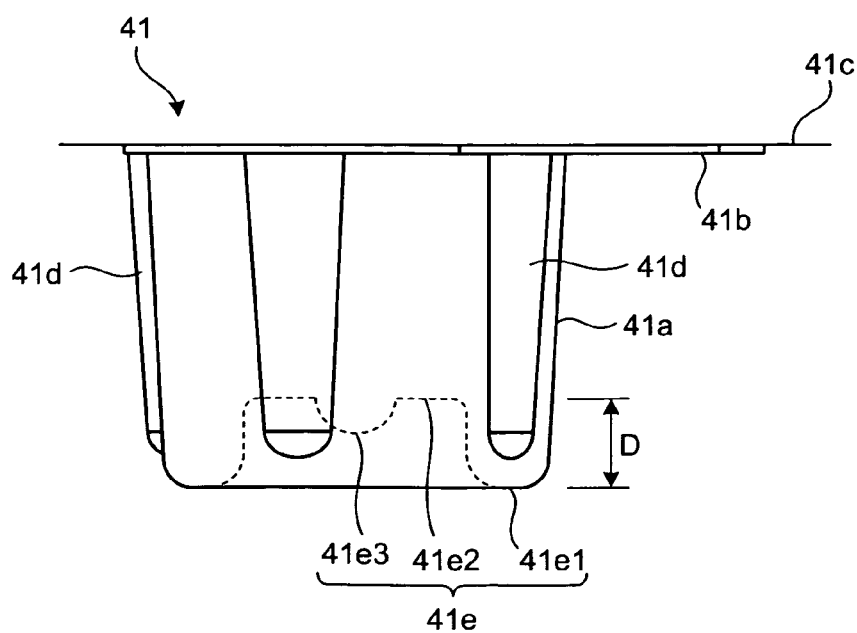
FIG. 7 is similarly a side view showing the side of the container case.

As shown in FIGS. 6 and 7, the blister pack 41 includes a cylindrical portion 41a having a bottom and a tab portion 41b having a tongue shape provided on part of the upper edge of the opening of the cylindrical portion 41a, a rim portion 41c provided on the upper edge of the cylindrical portion 41a and the outer circumference of the tab portion 41b, and plural projection portions 41d having nearly half-columnar shapes and projecting from interior of the cylindrical portion 41a toward outside.

The cylindrical portion 41a has a bottom surface 41e, and the bottom surface 41e includes an outer bottom surface 41e1 provided at the outer circumference side of the cylindrical portion 41a and an inner bottom surface 41e2 provided nearly at the center of the outer bottom surface 41e1. The inner bottom surface 41e2 is formed in a disk shape having a predetermined radius, and the outer bottom surface 41e1 includes a bottom surface projecting from the position of the inner bottom surface 41e2 toward outside of the cylindrical portion 41a (in the opposite direction to the opening direction) and is formed in a doughnut shape with a lower surface having a predetermined width. As shown in FIG. 7, a level difference D is produced between the outer bottom surface 41e1 and the inner bottom surface 41e2. Further, a holding portion 41e3 having a nearly semispherical shape that is recessed from the position of the inner bottom surface 41e2 toward the outer bottom surface 41e1 is provided at the center of the inner bottom surface 41e2. The holding portion 41e3 is for holding the rear end of the dome shape that forms the barrel portion cover 11b of the capsule endoscope 2, and provided with a projection portion 41e4 having a cross shape toward the opening direction for enabling uniform sterilization of the entire rear end portion by the penetration of sterilizing gas in the rear end portion of the barrel portion cover 11b that is held in line contact. The projection portion 41e4 may include plural projections for holding the rear end portion of the capsule endoscope 2 in point contact, respectively.

The tab portion 41b is a plate-like member having a upper surface of nearly triangular shape, and configured, as shown in FIG. 5, to be in contact with a tab portion 42b of the inner lid portion 42, which will be described later. The rim portion 41c has a predetermined width and is provided in a step-like shape higher by one step on the upper edge of the opening of the cylindrical portion 41a and the outer circumference of the tab portion 41b for suppressing the movement of the tab portion of the inner lid portion 42 in contact with the tab part 41b. Further, the height of the rim portion 41c is equal to or more than the thicknesses of the tab portion 42b and a rim portion 42c of the inner lid portion 42 in contact with the tab part 41b, and enables the attachment of the sterilizing sheet 43 to the upper surface of the rim portion 41c when the inner lid portion 42 is accommodated within the blister pack 41.

The projection portion 41d includes a projection having a nearly half-columnar shape provided along the longitudinal direction of the cylindrical portion 41a, and is configured so that the diameter of the upper end (opening side of the cylindrical portion 41a) is the largest, and the smaller the diameter gradually becomes, the nearer the lower end (bottom surface 41e side). The projection portions 41d having the same shape are arranged at nearly equal intervals along the longitudinal direction of the cylindrical portion 41a. In the projection portion 41d, the upper end opens and the lower end forms a bottom surface having a half-dome shape. In this embodiment, five projection portions 41d are respectively arranged at nearly equal intervals on the outer circumference of the cylindrical portion 41a.

As shown in FIGS. 8 and 9, the inner lid portion 42 includes a cylindrical portion 42a having a bottom and a tab portion 42b having a tongue shape provided on part of the upper edge of the opening of the cylindrical portion 42a, a rim portion 42c provided on the upper edge of the cylindrical portion 42a continuously from the tab portion 42b, and plural projection portions 42d having nearly half-columnar shapes and projecting from inside of the cylindrical portion 42a toward outside.

As shown in FIGS. 8 to 12, the cylindrical portion 42a has a bottom surface 42e, and a projecting portion 42e1 having a hole for holding the capsule endoscope 2 is provided at the center of the bottom surface 42e. The projecting portion 42e1 is formed in a nearly cylindrical shape having a convex section with an upper surface projecting from the position of the bottom surface 42e toward inside of the cylindrical portion 42a (in the opening direction), and the inner diameter thereof is slightly larger than the outer diameter of the capsule endoscope 2. On the inner circumference of the projecting portion 42e1, plural, in this embodiment, four linear projections 42e2 are formed along the longitudinal direction toward the opening of the projecting portion 42e1. Further, at the upper surface side of the projecting portion 42e1, a step portion 42e3 is provided and the inner diameter of the step portion 42e3 is smaller than the inner diameter of the projecting portion 42e1 at the opening side thereof. As shown in FIG. 12, when the inner lid portion 42 is accommodated within the blister pack 41, the bottom surface 42e including the projecting portion 42e1 of the cylindrical portion 42a and the inner bottom surface 41e2 including the holding portion 41e3 of the blister pack 41 form a holding space region 40a according to the invention so as to accommodate and hold the capsule endoscope 2.

In this embodiment, as shown in FIGS. 9 and 12, when the front cover 11a side of the capsule endoscope 2 is inserted into the projecting portion 42e1, in order to avoid contact of the mirror finish portion 11a1 within the range of the dashed lines a-a with component parts of the projecting portion 42e1 including the projections 42e2 and the step portion 42e3, the projections 42e2 hold part of the barrel portion cover 11b of the sealed container 11 in line contact, and the leading edge of the step portion 42e3 holds part of the front cover 11a in line contact. These projections 42e2 are not limited to those linearly formed along the longitudinal direction of the projecting portion 42e1, and plural projection portions may be provided in the projecting portion 42e1, for example, and part of the barrel portion cover 11b of the sealed container 11 may be held in point contact, respectively.

The tab portion 42b is a plate-like member having an upper surface of nearly triangular shape substantially smaller than the tab portion 41b, and formed integrally with the rim portion 42c provided on the upper edge of the opening of the cylindrical portion 41a, as shown in FIGS. 8 and 11. The tab portion 42b is configured to be in contact with the tab portion 41b of the blister pack 41 when the inner lid portion 42 is accommodated within the blister pack 41. Further, the rim portion 42c is provided on the upper edge of the opening of the cylindrical portion 42a and configured to be in contact with the upper edge of the opening of the blister pack 41 when the inner lid portion 42 is accommodated within the blister pack 41. As described above, the thicknesses of these tab portion 42b and rim portion 42c are formed equal to or less than that of the rim portion 41c of the blister pack 41. When the inner lid portion 42 is accommodated within the blister pack 41, the motion of the tab portion 42b is restricted by the rim portion 41c within the range of the width of the tab part 41b. When the sterilizing sheet 43 is attached to the upper surface of the rim portion 41c, the entire inner lid portion 42 including these tab portion 42b and rim portion 42c is accommodated within the blister pack 41.

The projection portion 42d includes a projection having a nearly half-columnar shape provided along the longitudinal direction of the cylindrical portion 42a. The respective projection portions are arranged at nearly equal intervals along the longitudinal direction of the cylindrical portion 42a. In the projection portion 42d, the upper end opens and the lower end forms a bottom surface having a half-dome shape. In the embodiment, five projection portions 42d are arranged at nearly equal intervals on the circumference of the cylindrical portion 42a, respectively. These projection portions 42d prevent the looseness of the inner lid portion 42 within the blister pack 41 because the projection portions are respectively formed so that the most projecting portions of the projection portions 42d are in contact with the inner circumference of the cylindrical portion 41a in positions where they do not face the projection portions 41d of the blister pack 41, when the inner lid portion 42 is accommodated within the blister pack 41 and tab portion 41b and the tab portion 42b are in contact with each other.

As shown in FIGS. 5, 11, and 12, paths 40b of air gap according to the invention are formed between the inner circumference of the projection portions 41d of the blister pack 41 and the outer circumference of the cylindrical portion 42a of the inner lid portion 42, and thereby, the sterilizing gas penetrated from outside via the sterilizing sheet 43 can pass through them. Further, the paths 40b and the holding space region 40a are in communication with each other, and thereby, the sterilizing gas passing the paths 40b can reach the holding space region 40a.

Figure 2:
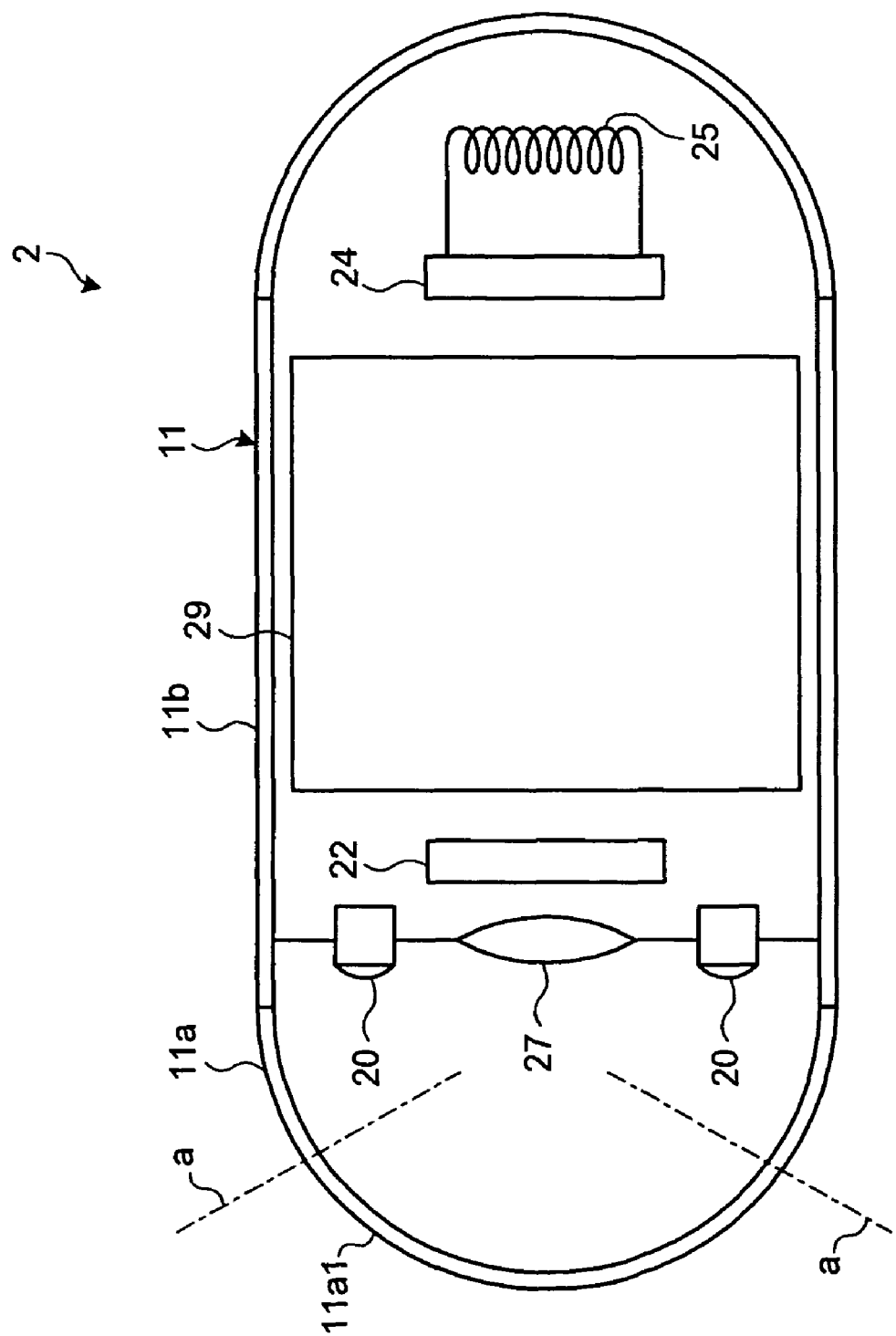
FIG. 2 is a side sectional view showing a schematic configuration of a capsule endoscope shown in FIG. 1.
Figure 13:
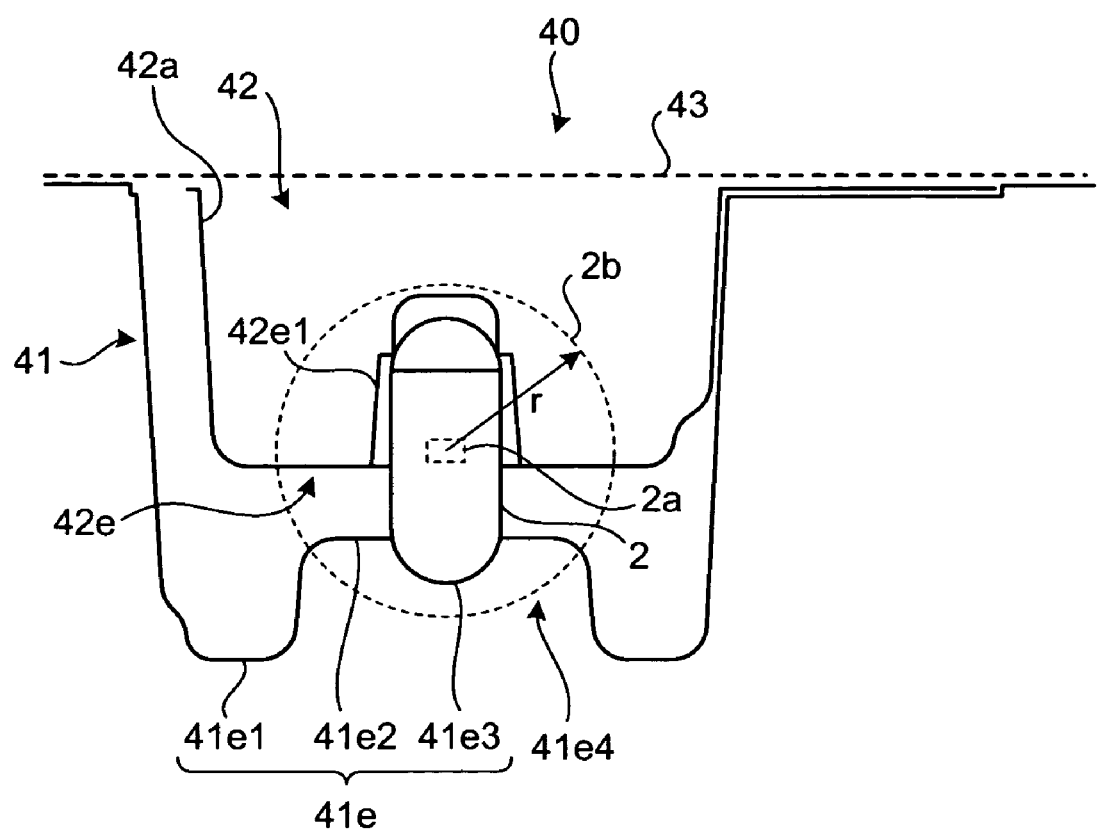
FIG. 13 is a sectional view for explanation of a power supply operable range similarly to FIG. 11.

Further, as shown in FIG. 13, the capsule endoscope 2 has a reed switch 2a for power supply that performs on/off operation according to the external magnetic field within, and indicates to the outside that the reed switch 2a is turned on and power is supplied to the respective function executing units by the blinking of the LED 20 shown in FIG. 2. The reed switch 2a is provided nearly at the center in the longitudinal direction of the capsule endoscope 2, and has a spherical power supply operable range 2b within radius "r" from the reed switch 2a where the reed switch turns on when a permanent magnet (not shown) approaches and a predetermined magnetic force is applied. In this embodiment, for example, the diameters of the bottom surface 41e of the blister pack 41 and the bottom surface 42e of the inner lid portion 42 are made longer than the diameter 2r of the power supply operable range 2b. Further, in the embodiment, when the capsule endoscope 2 is held by the holding portion 41e3 of the blister pack 41 and the projecting portion 42e1 of the inner lid portion 42, the power supply operable range 2b contains the inner bottom surface 41e2 and the holding portion 41e3 and is set within the range of the heights of the outer bottom surface 41e1 and the inner bottom surface 41e2, and contains the projecting portion 42e1 and is set within the range of the height of the cylindrical portion 42a.

Accordingly, when used, it is possible that the sterilizing sheet 43 is separated from the container case 40, a magnetic body (magnet) is accommodated inside of the cylindrical portion 42a of the inner lid portion 42, the reed switch is turned on by the magnetic field of the accommodated magnetic body, and the blinking state of the LED 20 can be confirmed from the transparent or translucent projecting portion 42e1. That is, the projecting portion 42e1 has a function of facilitating the confirmation of blinking of the LED other than the holding and protecting functions of the capsule endoscope 2.

Further, the capsule endoscope 2 has a reed switch for power supply (which will be described later) that performs on/off operation according to the external magnetic field within, and has a function of indicating to the outside that the reed switch is turned on and power is supplied to the respective function executing units by the lighting of the LED 20 shown in FIG. 2. Accordingly, in this embodiment, when used, the reed switch is switched from the off-state to the on-state as the power supply state using a power supply starter for capsule endoscope 51 (hereinafter, simply referred to as "power supply starter") as shown in FIGS. 14 and 15.

The power supply starter 51 includes a tab portion 51a provided at the upper part thereof and a cylindrical portion 51b having a cylindrical shape provided at the lower part, and these tab portion 51a and cylindrical portion 51b are integrally formed. Further, a hole portion 51c that penetrates the center of the tab portion 51a as a confirming unit according to the invention is provided along the longitudinal direction of the cylindrical portion 51b.

Figure 14:
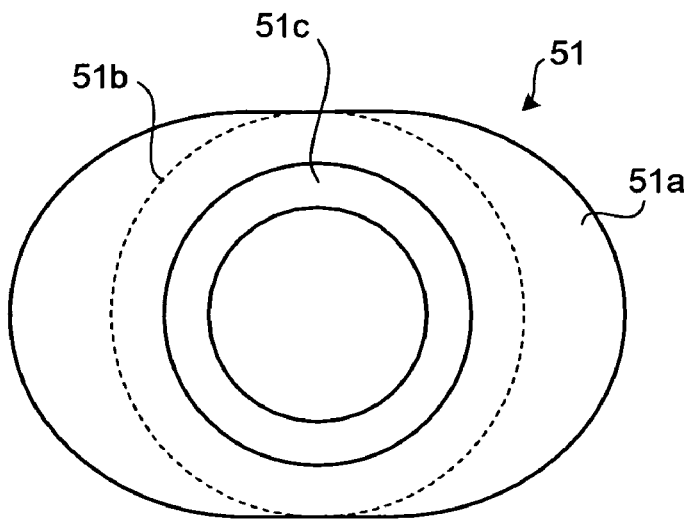
FIG. 14 is a top view showing the top of a power supply starter for capsule endoscope according to the first embodiment.
Figure 15:
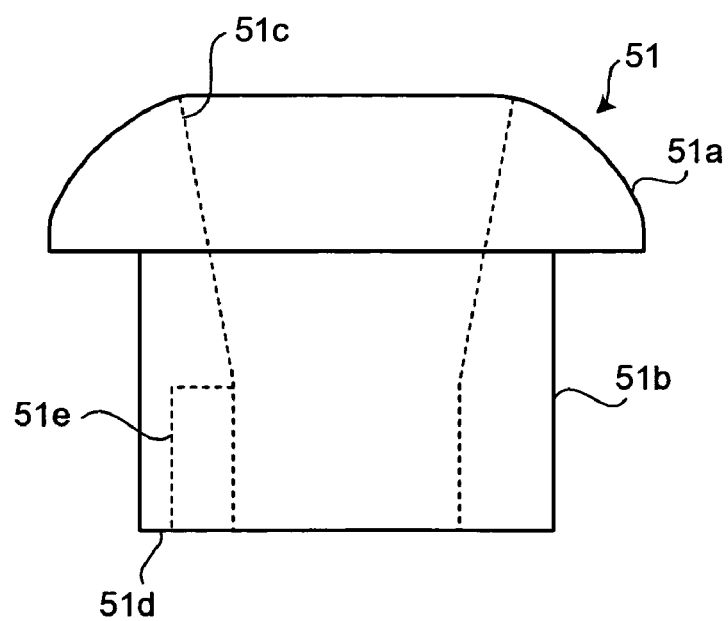
FIG. 15 is similarly a side view showing the side of the power supply starter for capsule endoscope.
Figure 16:
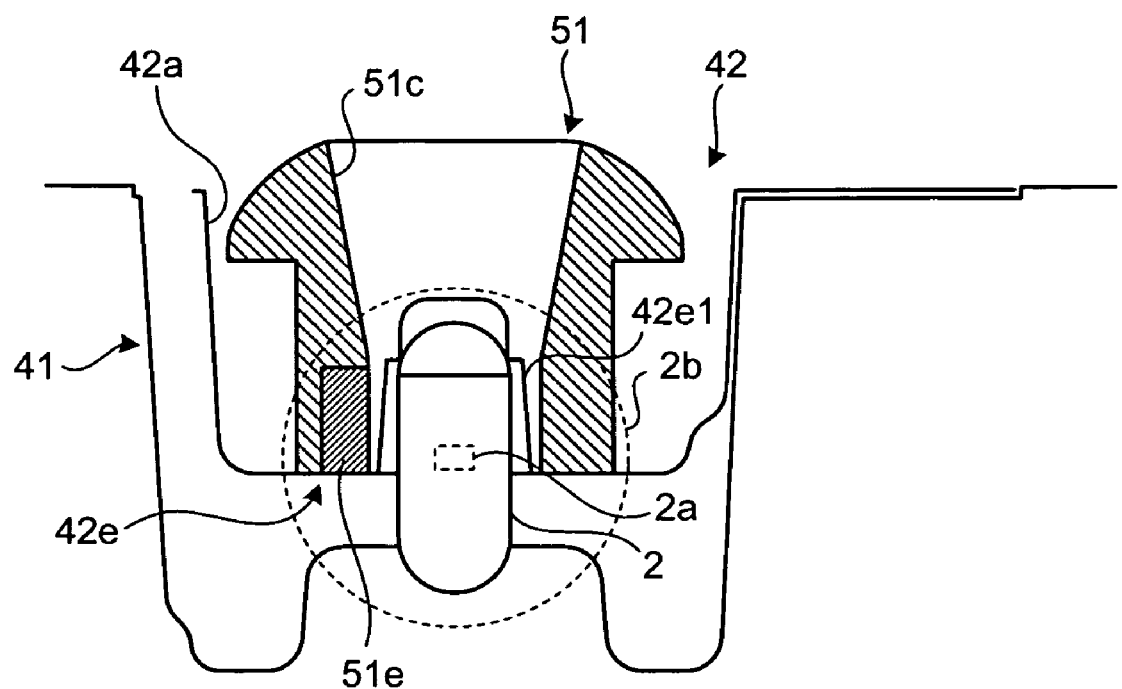
FIG. 16 is a sectional view showing B-B section of FIG. 11 when the power supply starter for capsule endoscope according to the first embodiment is mounted.

As shown in FIGS. 14 and 15, the tab portion 51a has an upper surface formed in a nearly elliptical shape and a side surface formed in a nearly trapezoidal shape. Further, the cylindrical portion 51b has a magnetic body 51e provided inside at the inner wall side of a bottom surface 51d. FIG. 16 is a sectional view showing B-B section of FIG. 11 when the power supply starter 51 is mounted. In FIG. 16, in the hole portion 51c, the diameter at the bottom surface 51d side is made slightly larger than the diameter of the projecting portion 42e1 of the inner lid portion 42, and the diameter of the hole portion 51c is formed larger from the middle of the hole portion 51c upward in a tapered form. Further, the length of the hole portion is made longer than the length of the projecting portion 42e1 of the inner lid portion 42. Therefore, when the sterilizing sheet 43 is separated from the container case 40, the power supply starter 51 can be engaged so as to cover the entire projecting portion 42e1 from the upper surface side of the inner lid portion 42. The diameter of the hole portion 51c becomes larger upwardly in a tapered form for facilitating the confirmation when the LED 20 of the capsule endoscope 2 lights. Further, contrary, when the diameter of the hole portion 51c is made smaller upwardly in a tapered form and the power supply starter 51 is formed in dark color, the operator can easily confirm the lighting of the LED 20 from the opening of the hole portion 51c.

The outside diameter (hereinafter "diameter") of the cylindrical portion 51b is formed smaller than the diameter 2r of the power supply operable range 2b of the reed switch 2a, and the magnetic body 51e provided within the bottom surface 51b is formed by a square magnet having a predetermined size that is curved in the same manner as the inner wall of the bottom surface 51b, for example. When the power supply starter 51 is engaged so as to cover the projecting portion 42e1 of the inner lid portion 42, the magnetic body 51e enters the power supply operable range 2b and turns the reed switch 2a on by the magnetic field of the magnetic body 51e, and thereby, the lighting state of the LED 20 can be confirmed from the hole portion 51c.

Figure 17:
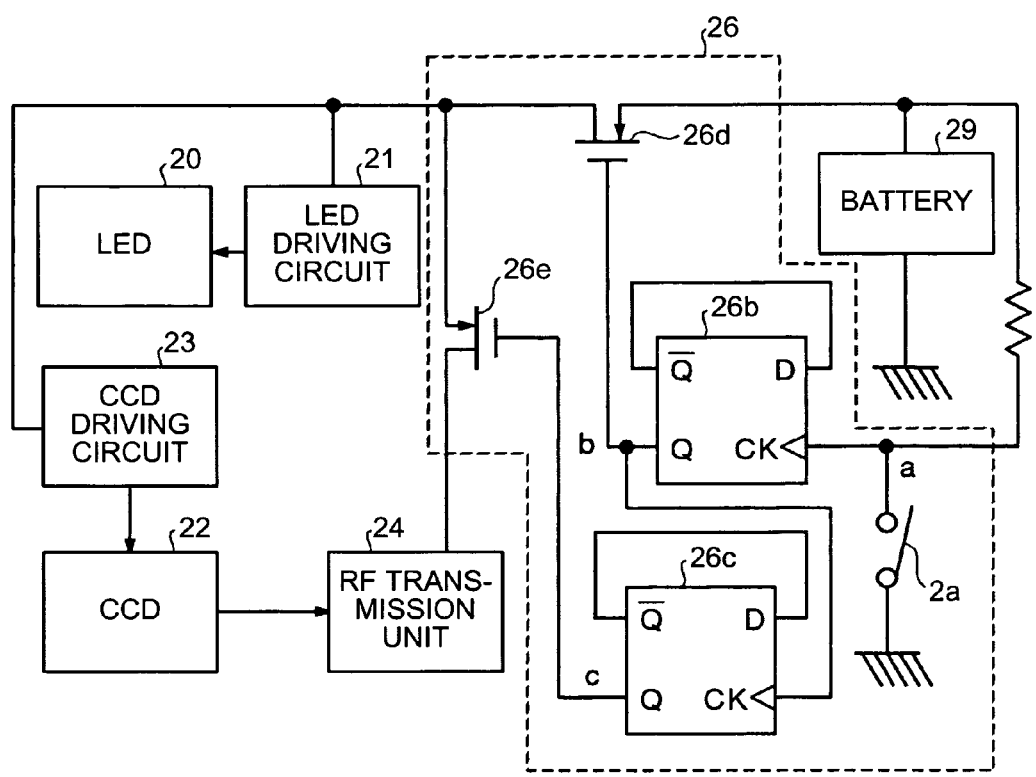
FIG. 17 is a circuit diagram showing a circuit configuration of the system control circuit of the capsule endoscope according to the first embodiment shown in FIG. 3.

Next, the circuit configuration of the system control circuit 26 of the capsule endoscope 2 according to First embodiment shown in FIG. 3 will be described using a circuit diagram in FIG. 17. In FIG. 17, the system control circuit 26 includes a reed switch 2a as a switch for power supply with one end grounded and the other end connected to a latch circuit, which will be described later, flip-flops 26b, 26c, and FETs (field-effect transistors) 26d, 26e connected to the flip-flops 26b, 26c and functioning as switch elements. The reed switch 2a performs on/off operation according to a magnetic field applied from outside, the flip-flops 26b, 26c sequentially set the FETs 26d, 26e to on-state when clocks enter by the on/off operation of the reed switch 2a.

That is, when a magnetic field is applied from outside, the reed switch 2a performs on-operation and becomes from high (H) level to low (L) level at point a in the drawing. Further, when the magnetic field is no longer applied, the reed switch 2a performs off-operation and turns from L-level to H-level at point a. Through the operation, a clock enters CK terminal of the flip-flop 26b. In the flip-flop 26b, a signal dividing the rising edge from L-level to H-level at point a is Q-output (signal at point b). The FET 26d turns on when the Q-output of the flip-flop 26b is at L-level, power is supplied from the battery 29 to LED driving circuit 21 and the CCD driving circuit 23 and they are activated, driving of the LED 20 and CCD 22 is enabled, and the LED 20 lights.

Then, when a magnetic field is applied from outside, H-level turns to L-level at point a again. By the operation, the Q-output of the flip-flop 26b turns to H-level (signal at point b), and the FET 26d turns off, the power supply to the entire circuit is stopped, and the LED 20 is turned off. Further, then, when a magnetic field is applied from outside, H-level turns to L-level at point "a" again. By the operation, the Q-output of the flip-flop 26b turns to L-level (signal at point b), and the FET 26d turns on, power is supplied from the battery 29 to the LED driving circuit 21 and the CCD driving circuit 23, and the LED 20 turns on. Thus, the FET 26d turns on by so-called toggle operation when a magnetic field is applied to the reed switch 2a.

Further, the Q-output of the flip-flop 26b enters a clock terminal of the flip-flop 26c having a function for activating only the RF transmission unit 24. In the flip-flop 26c, a signal dividing the rising edge from L-level to H-level at point b is Q-output (signal at point c). Therefore, the FET 26e turns on by the on-operation of the reed switch 2a due to the second magnetic field application, and turns off by the on-operation of the reed switch 2a due to the fourth magnetic field application. Accordingly, at the time of third magnetic field application, both the FETs 26d and 26e turn on, and power is also supplied from the battery 29 to the RF transmission unit 24. In this embodiment, it is preferable, for example, that the above described first magnetic field application is set at the time of factory shipment, and all of the LED 20, the CD 22, and the RF transmission unit 24 can be driven due to three magnetic field applications at the time of use for the examinee.

Figure 18:
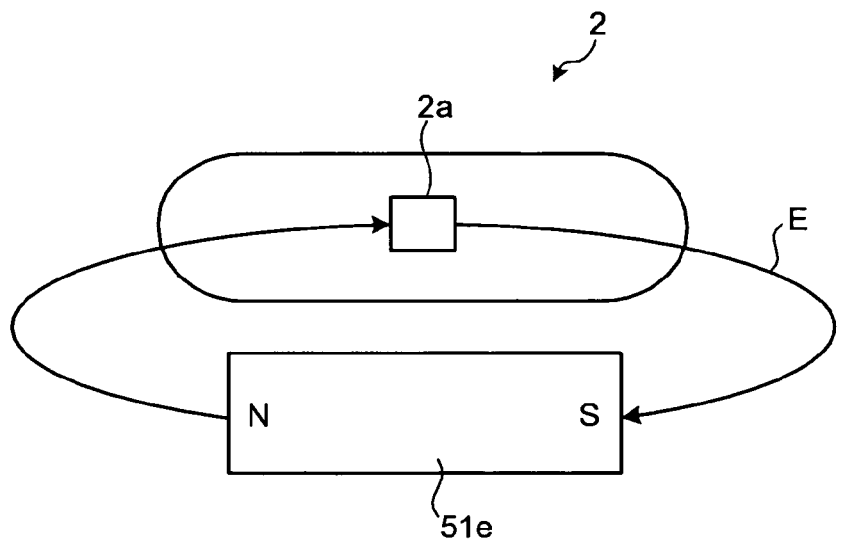
FIG. 18 is a schematic view showing the relationship between the magnetic field generated by a magnetic body shown in FIG. 16 and the capsule endoscope.

In order to perform the above described operation, as shown in FIG. 18, it is necessary that the reed switch 2a cuts magnetic field E generated from the magnetic body 51e, however, if the direction of the magnetic force is different, the magnetic force does not acts on the reed switch 2a and the reed switch 2a is not turned on. Accordingly, in this embodiment, the power supply starter 51 is turned to 90 degrees at the maximum in the circumferential direction of the capsule endoscope 2 while the capsule endoscope 2 is held in the projecting portion 42e1, and thereby, the reed switch 2a is sure to cut the magnetic field E, and the magnetic force of the magnetic body 51e acts on the reed switch 2a, power is supplied to the reed switch 2a, and the LED 20 is turned on.

Figure 19:
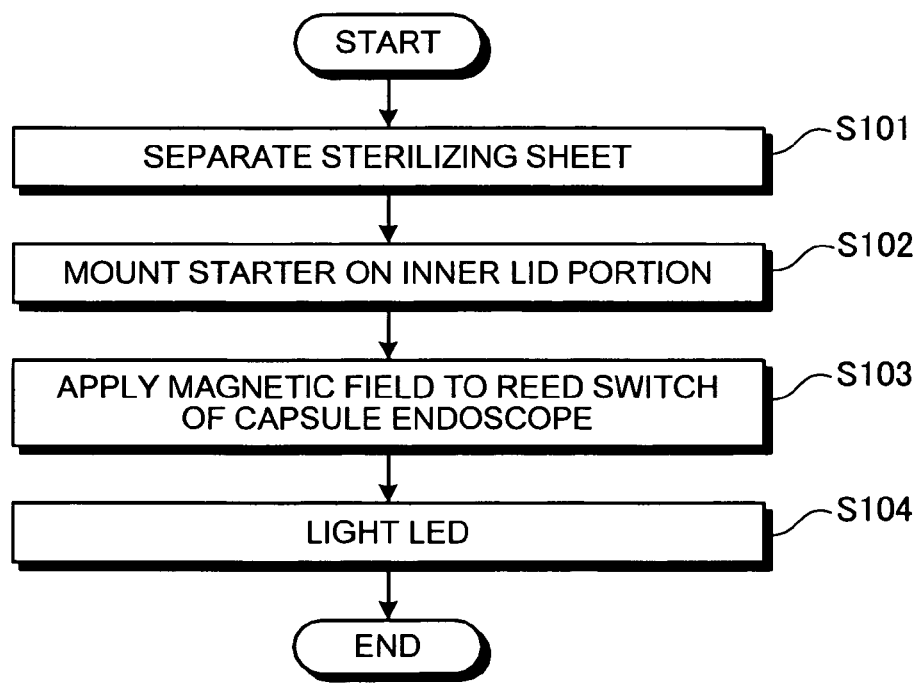
FIG. 19 is a flowchart for explanation of the power supply start operation of the capsule endoscope shown in FIG. 17.

Next, the power supply start operation of the capsule endoscope 2 will be described based on a flowchart of FIG. 19. In the chart, first, before the capsule endoscope 2 is used, the sterilizing sheet 43 is separated from the sterilized container case 40 (step 101) as shown in FIG. 5, and the power supply starter 51 is inserted into the inner lid portion 42 and mounted on the projecting portion 42e1 (step 102). Then, in the mounted condition, an operator such as a nurse grasps the tab portion 51a of the power supply starter 51, turns the power supply starter 51 to 90 degrees at the maximum in the circumferential direction of the capsule endoscope 2, and applies a magnetic field to the reed switch 2a of the capsule endoscope 2 (step 103). Thus, when the magnetic field is applied to the reed switch 2a by the power supply starter 51, the reed switch 2a turns on and power from the battery 29 is supplied to the LED driving circuit 21, the CCD driving circuit 23, and the RF transmission unit 24, and thereby, the respective functions are driven and lighting of the LED 20 as well as imaging of the CCD 22 and transmission of image information of the RF transmission unit 24 can be performed (step 104). The operator can confirm the lighting of the LED 20 from the opening of the hole portion 51c.

Thus, in this embodiment, the reed switch as a switch for power supply within the capsule endoscope can be switched from off-state to on-state (power supply state) by mounting the power supply starter with the magnetic body on the inner lid portion by which the capsule endoscope is held and applying a magnetic field to the capsule endoscope by the magnetic body from outside of the inner lid portion, and therefore, the start to drive the respective functions of the capsule endoscope can be performed with arbitrary timing, for example, immediately before the use for the examinee, and the consumption of power accumulated within the capsule endoscope can be suppressed.

Second Embodiment

Figure 20:
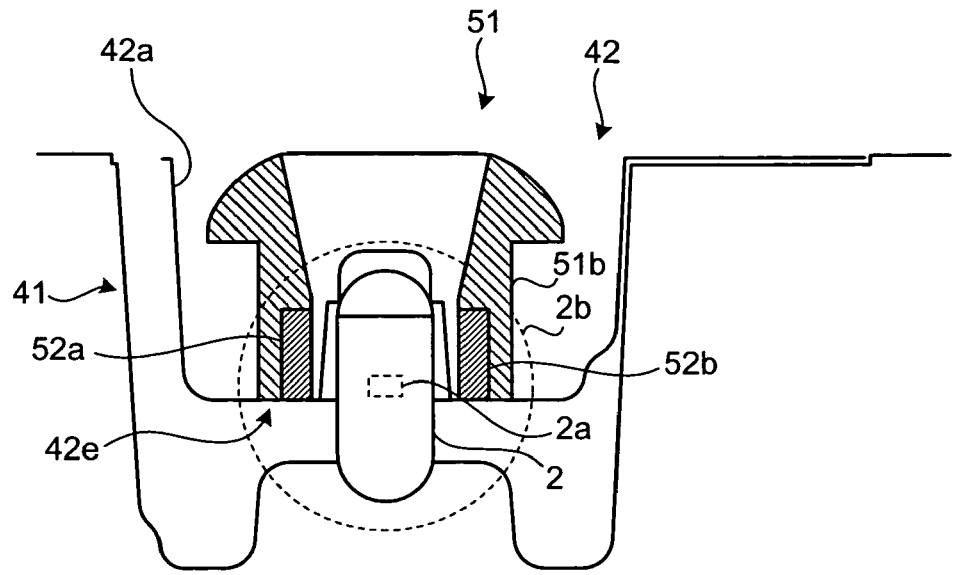
FIG. 20 is a sectional view showing B-B section of FIG. 11 when a power supply starter for capsule endoscope according to a second embodiment is mounted.

FIG. 20 is a sectional view showing B-B section of FIG. 11 when a power supply starter according to a second embodiment is mounted. In FIG. 20, in this embodiment, plural (two in the embodiment) magnetic bodies 52a, 52b are provided in opposed positions of the cylindrical portion 51b of the power supply starter 51. For these magnet bodies 52a, 52b, magnetic bodies having thinner thicknesses and weaker magnetic forces, e.g., about the half magnetic force, than the magnetic body 51e shown in First embodiment are used.

Figure 21:
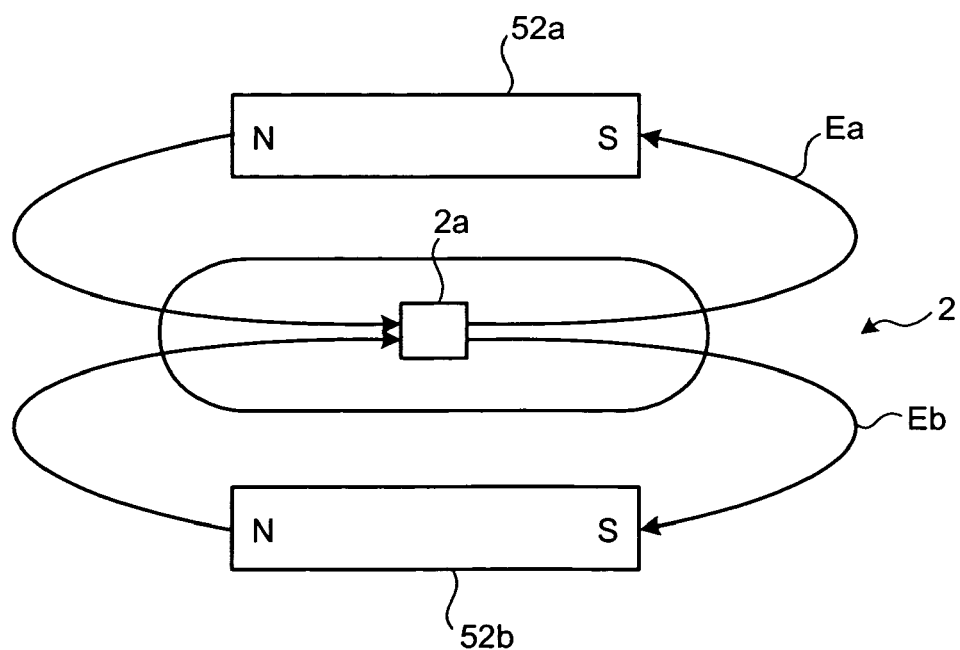
FIG. 21 is a schematic view showing the relationship between the magnetic field generated by a magnetic body shown in FIG. 20 and the capsule endoscope.

In the embodiment, as shown in FIG. 21, in order to supply power for allowing the driving of the above described LED 20, CCD 22, and RF transmission unit 24, the reed switch 2a are configured to cut magnetic fields Ea, Eb generated from the magnetic bodies 52a, 52b as shown in FIG. 18. Accordingly, the polarity of the magnetic bodies 52a, 52b is set in the same direction, for example, N-pole is at the bottom surface 42e of the inner lid portion 42 and S-pole is at the upper side, and therefore, the magnetic fields Ea, Eb in the same direction are constantly generated from the magnetic bodies 52a, 52b. When the power supply starter 51 is turned to 90 degrees at the maximum in the circumferential direction of the capsule endoscope 2, the reed switch 2a surely cuts the magnetic fields Ea, Eb, and thereby, the magnetic forces of the magnetic bodies 52a, 52b act on the reed switch 2a and power is supplied to the reed switch 2a, and LED 20 can be turned on. Note that the number of magnetic bodies is not limited to two in the embodiment, but may be four or more.

Thus, in the embodiment, plural magnetic bodies are provided in opposed positions of the cylindrical portion of the power supply starter and the directions of the magnetic fields applied to the reed switch are made in the same direction, and thereby, the same effect as that of the first embodiment can be obtained, magnetic bodies smaller than the magnetic body used in the power supply starter in the first embodiment can be used, and the downsizing of the entire power supply starter can be realized.

Third Embodiment

Figure 22:
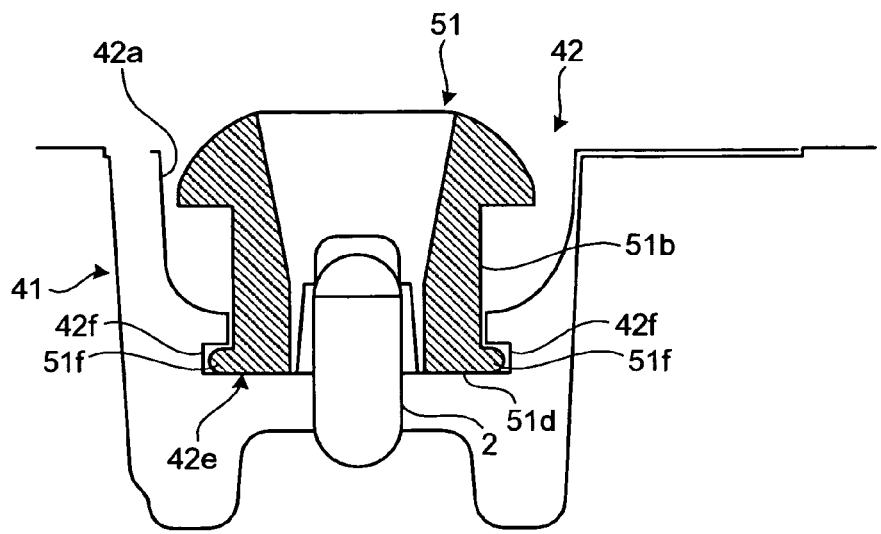
FIG. 22 is a sectional view showing B-B section of FIG. 11 when a power supply starter for capsule endoscope according to a third embodiment is mounted.

FIG. 22 is a sectional view showing B-B section of FIG. 11 when a power supply starter according to a third embodiment is mounted. In FIG. 22 and subsequent FIG. 23, the description of magnetic body will be omitted. In FIG. 22, the inner lid portion 42 provides a groove 42f on the side end part of the bottom surface 42e of the cylindrical portion 42a. The groove 42f forms one lateral groove in an endless shape having a C-shaped section. Further, the power supply starter 51 provides a projection 51f on the side end part of the bottom surface 51d of the cylindrical portion 51b. The projection 51f forms one projection in an endless shape having a D-shaped section formed engageable with the above described groove 42f. The groove 42f and the projection 51f form engagement portions according to the invention.

Since the inner lid portion 42 is formed in a thin form by a material of polypropylene having flexibility as described above, when the projection 51f contacts at the time of mounting the power supply starter 51, the contact part deforms outward and enables the projection 51f to engage with the groove 42f. Further, the section of the projection 51f is formed to have a D-shaped section and the groove 42f is formed to have a C-shaped section and slight looseness is provided when the projection 51f engages with the groove 42f, and therefore, the power supply starter 51 can be easily turned in the circumferential direction of the capsule endoscope 2. At the time of taking out the capsule endoscope 2, the operator can take out the capsule endoscope 2 with the engaged inner lid portion 42 when the operator takes out the power supply starter 51 from inside of the blister pack 41.

Thus, in the embodiment, the groove portion is provided in the inner lid portion and the projection engaging with the groove is provided in the power supply starter, and therefore, the same effect as that of First embodiment can be exerted and the capsule endoscope can be easily taken out from the container case with the inner lid portion.

Figure 23:
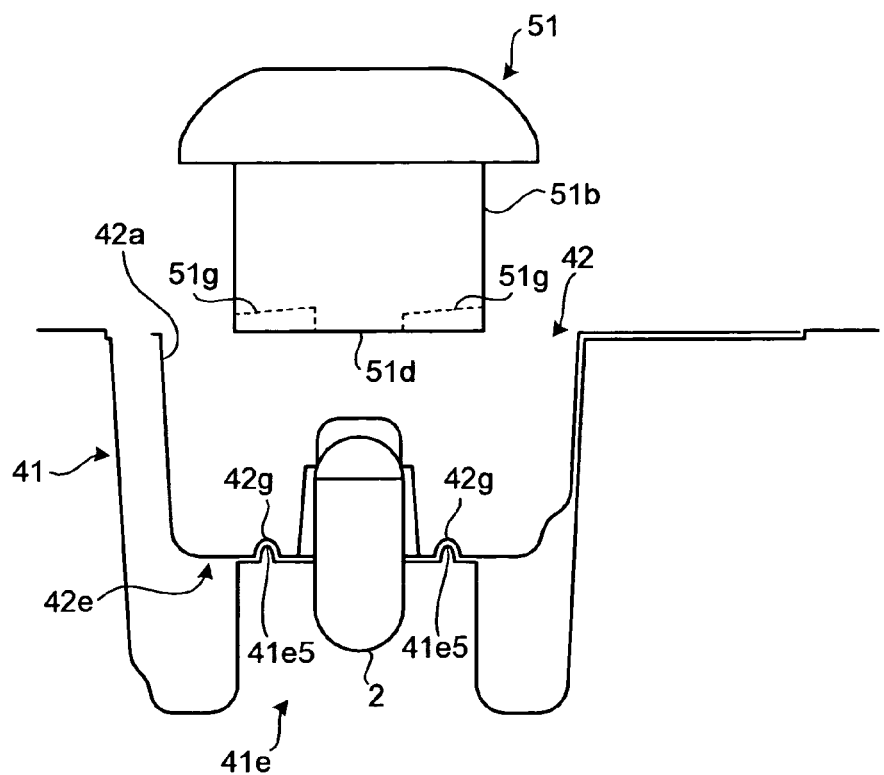
FIG. 23 is a sectional view showing B-B section of FIG. 11 when a power supply starter according to a first modification is mounted.

FIG. 23 is for explanation of a first modification of the blister pack 41, the inner lid portion 42, and the power supply starter 51, and a sectional view showing B-B section of FIG. 11 when a power supply starter is mounted. In FIG. 23, plural projections 41e5, 41e5 are provided in predetermined positions on the bottom surface 41e of the blister pack 41, and projections 42g, 42g having holes that fit the projections 41e5, 41e5 are provided on the bottom surface 42e of the inner lid portion 42. In the condition before use, the projections fit each other for fixing the lid part 42 within the blister pack 41.

In the cylindrical portion 51b at the bottom surface 51d side of the power supply starter 51, grooves 51g, 51 into which the projections 42g, 42g of the inner lid portion 42 can be inserted are provided to be directed upward. Both ends of the grooves 51g, 51g are formed in different heights, and one end is nearly equal to the height of the projections 42g, 42g and the other end is lower than the height of the projections 42g, 42g, for example, about the half thereof. Further, the lengths of the projections 42g, 42g are formed as lengths with which the power supply starter 51 can be turned 90 degrees at the maximum in the circumferential direction of the capsule endoscope 2.

In the configuration, the power supply starter 51 is inserted into the inner lid portion 42, and the projections 42g, 42g of the inner lid portion 42 are engaged with the grooves 51g, 51g. Then, the power supply starter 51 is turned in the circumferential direction of the capsule endoscope 2 (counterclockwise direction), power is supplied to a reed switch (not shown) as is the case of the above described embodiments. Furthermore, with the turn, the heights of the grooves 51g, 51g in positions in contact with the projections 42g, 42g become lower, the projections 42g, 42g are deformed downward, the fitting condition with the projections 41e5, 41e5 is released, and thereby, the inner lid portion 42 can be detached from the blister pack 41.

Thus, in First modification, projections fitting each other are provided in the blister pack and the inner lid portion and grooves for releasing the fitting are provided in the power supply starter, and therefore, the same effect as that of First embodiment can be exerted, the fitting of the blister pack and the inner lid portion can be easily released by the power supply starter, and the capsule endoscope can be easily taken out from the container case with the inner lid portion.

Figure 24:
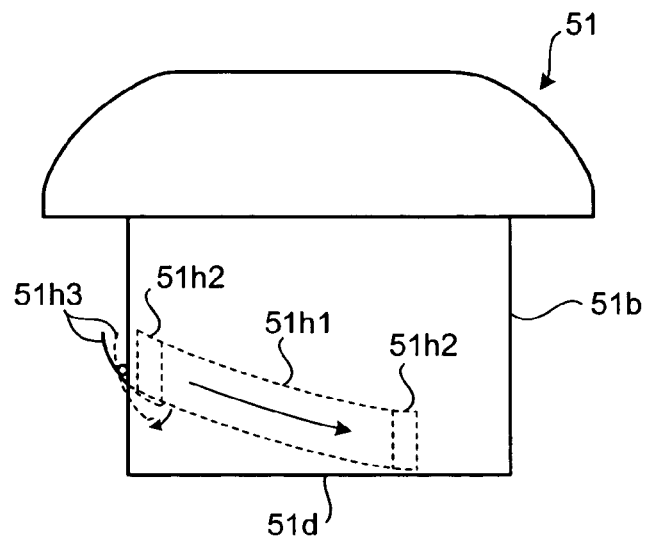
FIG. 24 is a side view showing the side of a power supply starter according to a second modification.

FIG. 24 is for explanation of a second modification of a power supply starter and a side view showing the side of the power supply starter. In FIG. 24, in the cylindrical portion 51b at the bottom surface 51d side of the power supply starter 51, a groove 51h1 for movably holding a magnetic body 51h2 and a claw portion 51h3 for inhibiting the magnetic body 51h2 are provided. In the groove 51h1, the base end for inhibiting the magnetic body 51h2 is higher at the tab portion 51a side, and the terminal end is lower at the bottom surface 51d side. Further, the length of the groove 51h1 is formed as a length with which magnetic body 51h2 can be turned to 90 degrees at the maximum in the circumferential direction of the capsule endoscope 2. The groove 51h1 forms a movement portion according to the invention, and the claw portion 51h3 forms an inhibiting portion according to the invention, respectively.

The claw portion 51h3 is provided in the cylindrical portion 51b at the base end side of the groove 51h1, and typically formed at the base end side of the groove 51h1 for inhibiting the magnetic body 51h2. For example, when inserted into the inner lid portion 42 as shown in FIG. 42, one end of the claw portion 51h3 contacts the cylindrical portion 51b and the other end moves in the direction of an arrow in the drawing and releases the inhibition condition of the magnetic body 51h2. When the inhibition condition is released, the magnetic body 51h2 slidingly moves in the groove 51h1 naturally due to attraction force to the terminal end side. It is preferable that treatment with little friction is performed on the contact surface in the groove 51h1 with the magnetic body 51h2 so that the magnetic body 51h2 can move.

Thus, in the second modification, the groove for movably holding the magnetic body and the claw portion for inhibiting the magnetic body are provided in the power supply starter. When the power supply starter is inserted into the inner lid portion, the inhibition condition of the claw portion is released by the cylindrical portion and the magnetic body naturally moves in the groove and can be turned to 90 degrees at the maximum in the circumferential direction of the capsule endoscope 2, and therefore, the start to drive the respective functions of the capsule endoscope can be performed with arbitrary timing, for example, immediately before the use for the examinee, and the consumption of power accumulated within the capsule endoscope can be suppressed as is the case of First embodiment without turning the power supply starter.

Figure 25:
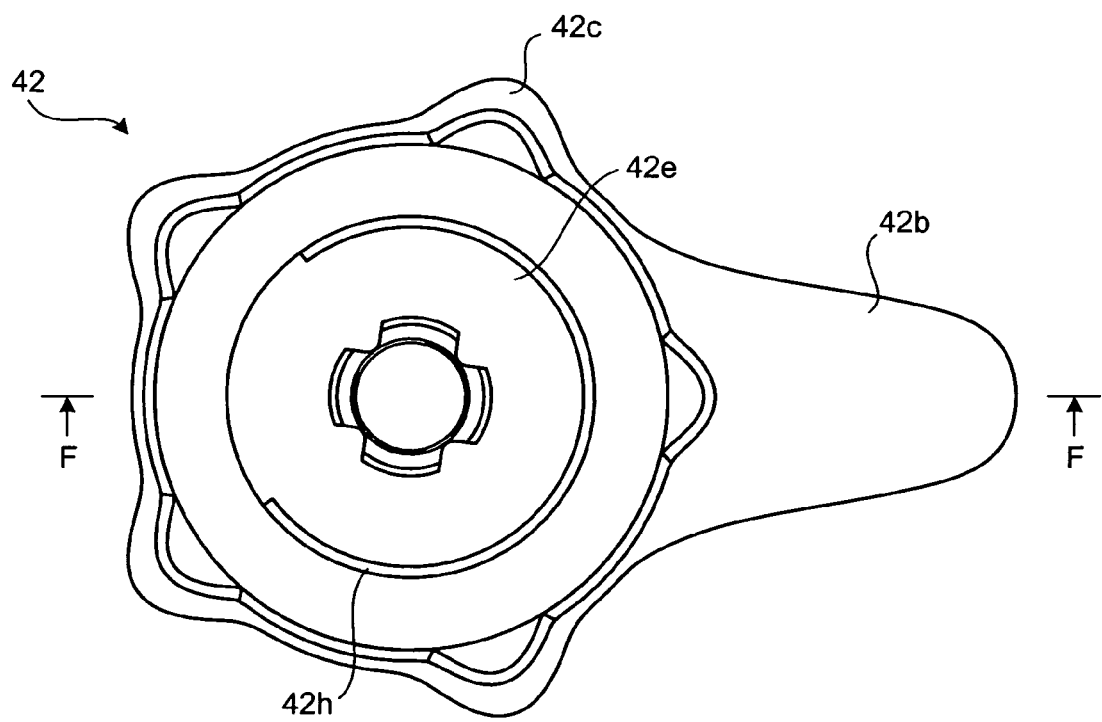
FIG. 25 is a top view showing the top of an inner lid portion according to a third modification.
Figure 26:
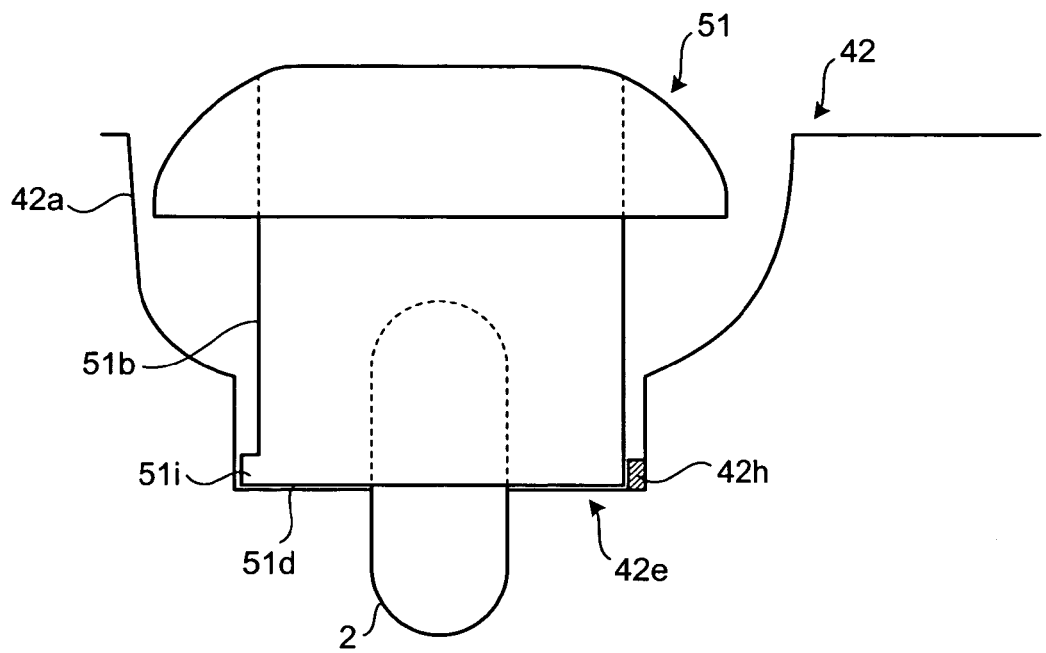
FIG. 26 is a sectional view showing F-F section of FIG. 25 when a power supply starter is mounted.

FIGS. 25 and 26 are for explanation of another Third modification of an inner lid portion and a power supply starter, and FIG. 25 is a top view showing the top of an inner lid portion according to Third modification and FIG. 26 is a sectional view showing F-F section of FIG. 25 when the power supply starter is mounted. In these drawings, a step portion 42h is provided at the bottom surface 42e side of the cylindrical portion 42a of the inner lid portion 42. The step portion 42h is provided in a belt-like form in a range of 270 degrees along the inner circumference of the cylindrical portion 42a.

Further, a projection 51i is provided at the bottom surface 51d side of the cylindrical portion 51b of the power supply starter 51. When the power supply starter 51 is inserted into the inner lid portion 42, the projection 51i enables the contact of the entire bottom surface 42e of the inner lid portion 42 with the entire bottom surface 51d of the power supply starter 51 in a position where no step portion 42h exists, and the power supply starter 51 can be turned to 90 degrees at the maximum in the circumferential direction of the capsule endoscope 2 in this condition.

Thus, in Third modification, the step portion is provided in the inner lid portion and the projection the turn of which is restricted by the step portion is provided in the power supply starter, and therefore, the operator can accurately turn the power supply starter inserted into the inner lid portion to 90 degrees, and thereby, the start to drive the respective functions of the capsule endoscope can be performed with arbitrary timing, for example, immediately before the use for the examinee, and the consumption of power accumulated within the capsule endoscope can be suppressed as is the case of the first embodiment.

Figure 27:
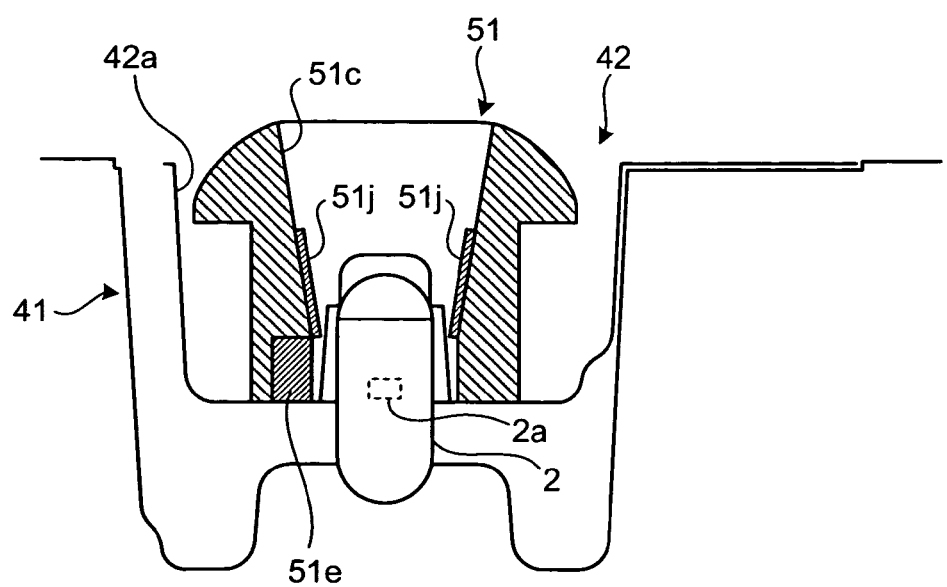
FIG. 27 is a sectional view showing B-B section of FIG. 11 when a power supply starter for capsule endoscope according to a forth modification is mounted.

FIG. 27 is a sectional view showing B-B section of FIG. 11 when a power supply starter for capsule endoscope according to a forth modification is mounted. In FIG. 27, in this modification, a reflection mirror 51j forming a confirming unit according to the invention with the hole portion 51c is provided in the tapered part of the hole portion 51c of the power supply starter 51, and the light from the lit LED is reflected upward of the hole portion 51c. Note that, in the modification, for example, the tapered part of the hole portion 51c may be formed to reflect the light like a reflection mirror by surface treatment.

Thus, in the forth modification, the reflection mirror is provided within the hole portion and the lighting of the LED is reflected upwardly, and therefore, the lighting of the LED can be easily confirmed visually by the operator, and the visibility for confirmation of the lighting of the LED can be improved.

Industrial Applicability

As described above, the container case of the capsule endoscope according to the invention is useful for a medical observation device inserted into a human body for observing a part to be examined, and especially, suitable for suppressing the consumption of the power accumulated within the capsule endoscope by performing the start to drive the respective functions of the capsule endoscope with arbitrary timing.

The invention claimed is:

1. A power supply starter system for a capsule endoscope, which has a switch being switched from an off-state to an on-state when applied with a magnetic field, the power supply starter system comprising:
   a container for accommodating and holding the capsule endoscope, the container having a projecting portion formed along a longitudinal direction of the capsule endoscope to hold the capsule endoscope and the switch therein, the container having a sheet for covering an opening of the container; and
   a power supply starter that comprises
      a cylindrical portion in which the projecting portion is inserted along the longitudinal direction when the sheet is removed from the container and the power supply starter is set in the container through the opening, and
      a magnetic body that applies the magnetic field to the switch when the projecting portion holding the capsule endoscope is inserted in the cylindrical portion, the magnetic body being provided on an inner wall of the cylindrical portion.

2. The power supply starter system for a capsule endoscope according to claim 1, wherein the container comprises an outer case and an inner lid, and
   the capsule endoscope is adapted to be held in a space between the outer case and the inner lid with both ends thereof inserted in holding portions provided in the outer case and the inner lid.

3. The power supply starter system for a capsule endoscope according to claim 2, wherein the inner lid and the outer case are provided with respective engagement portions that detachably engage with each other.

4. The power supply starter system for a capsule endoscope according to claim 3, wherein the capsule endoscope remains held by one of the inner lid and the other case when the inner lid and the outer case are detached from each other.

5. The power supply starter system for a capsule endoscope according to claim 3, wherein the engagement portions are projections provided in the side in which the power supply starter is set, and
   the power supply starter has grooves in the bottom thereof such that rotating the power supply starter with the power supply starter pressed against the inner lid causes the inner lid and the outer case to be detached from each other.

6. The power supply starter system for a capsule endoscope according to claim 2, wherein the inner lid has a projecting portion projecting from a bottom surface toward a power supply starter setting side and having a hole for holding the capsule endoscope, the projecting portion fitting into a hole portion of the power supply starter when the power supply starter is set in the inner lid, and
   the magnetic body is imbedded in the power supply starter such that a rotation of the power supply starter set in an engaged with the inner lid causes the change in the magnetic field generated thereby and applied to the switch.

7. The power supply starter system for a capsule endoscope according to claim 6, wherein the power supply starter is turned 90 degrees in the circumferential direction of the capsule endoscope.

8. The power supply starter system for a capsule endoscope according to claim 2, wherein the inner lid has a projecting portion projecting from a bottom surface toward a power supply starter setting side and having a hole for holding the capsule endoscope, the projecting portion fitting into a hole portion of the power supply starter when the power supply starter is set in the inner lid, and a part of the hole portion of the power supply starter which does not contact with the projecting portion of the inner lid is tapered.

9. The power supply starter system for a capsule endoscope according to claim 8, wherein the power supply starter has at least one reflection mirror on the tapered part of the hole portion thereof.

10. The power supply starter system for a capsule endoscope according to claim 8, wherein the power supply starter has at least a part of the tapered part of the hole portion thereof minor finished.

11. The power supply starter system for a capsule endoscope according to claim 1, wherein the power supply starter comprises:

a groove slanted off a circumferential direction of the cylindrical portion, the groove allowing the magnetic body to move therein, the groove having a first end and a second end positioned lower than the first end; and an inhibiting portion, provided at the first end of the groove, for inhibiting the magnetic body from starting sliding along the groove, the inhibiting portion is adapted to be arranged as to release the magnetic body when the power supply starter contacts the inner lid.

12. The power supply starter system for a capsule endoscope according to claim 1, wherein the power supply starter includes at least two magnetic bodies each pair of which are opposed to each other with the capsule endoscope being in between when the power supply starter is set in the container.

13. The power supply starter system for a capsule endoscope according to claim 12, wherein the at least two magnetic bodies are arranged such that directions of magnetic fields of the magnetic bodies which are applied to the switch are the same.

14. The power supply starter system for a capsule endoscope according to claim 1, further comprising a confirming unit for permitting a user to confirm the power supply state of the capsule endoscope.

15. The power supply starter system for a capsule endoscope according to claim 14, wherein the confirming unit includes a light emitting unit which emits light during an on-state of the power supply, the inner lid has a transparent portion for permitting a user to see the light, and the power supply starter has an opening through which the user can see the light.

16. The power supply starter system for a capsule endoscope according to claim 1, wherein the magnetic body is a magnet.

\* \* \* \* \*